(12) United States Patent
Cheng et al.

(10) Patent No.: US 9,022,782 B2
(45) Date of Patent: May 5, 2015

(54) DENTAL POSITIONING STENT, AND MANUFACTURING METHOD, USING METHOD AND COMPONENTS FOR THE SAME

(76) Inventors: Po-Kun Cheng, Taipei (TW); Chia-Yun Cheng, Taipei (TW); Chia-Yu Cheng, Taipei (TW); Chao-Hsiang Cheng, Taipei (TW)

( * ) Notice: Subject to any disclaimer, the term of this patent is extended or adjusted under 35 U.S.C. 154(b) by 6 days.

(21) Appl. No.: 13/302,255

(22) Filed: Nov. 22, 2011

(65) Prior Publication Data

US 2012/0135373 A1 May 31, 2012

(30) Foreign Application Priority Data

Nov. 26, 2010 (TW) ................................ 99140979 A

(51) Int. Cl.
| | | |
|---|---|---|
| *A61C 3/00* | (2006.01) | |
| *A61C 1/08* | (2006.01) | |
| *A61C 8/00* | (2006.01) | |
| *A61B 6/02* | (2006.01) | |
| *A61B 6/14* | (2006.01) | |
| *A61C 13/08* | (2006.01) | |
| *A61C 13/34* | (2006.01) | |

(52) U.S. Cl.
CPC .............. *A61C 1/084* (2013.01); *A61C 8/0089* (2013.01); *A61B 6/02* (2013.01); *A61B 6/14* (2013.01); *A61C 8/0051* (2013.01); *A61C 13/08* (2013.01); *A61C 13/34* (2013.01)

(58) Field of Classification Search
CPC ...... A61C 1/084; A61C 1/085; A61C 8/0051; A61C 9/002; A61B 6/02; A61B 6/14
USPC ...................... 433/72–75, 213–215
See application file for complete search history.

(56) References Cited

U.S. PATENT DOCUMENTS

| | | | | |
|---|---|---|---|---|
| 5,015,183 | A | | 5/1991 | Fenick |
| 5,782,636 | A | * | 7/1998 | Armstrong et al. ........... 433/165 |
| 5,927,982 | A | * | 7/1999 | Kruger .......................... 433/215 |

(Continued)

FOREIGN PATENT DOCUMENTS

| | | |
|---|---|---|
| DE | 102005023028 A1 | 11/2006 |
| EP | 1532939 A1 | 5/2005 |

(Continued)

OTHER PUBLICATIONS

China Office Action issued Jun. 3, 2013.
Japanese Patent Office, Office Action issued on Sep. 3, 2014, Japan.

*Primary Examiner* — Yogesh Patel

(57) ABSTRACT

A dental positioning stent for drilling an implant hole and a manufacturing method, a using method and components for the same are provided. The manufacturing method includes: slicing a tooth mold and a false tooth model along a preset slice plane; fixing two markers in the preset slice plane on two sides of the false tooth model respectively; covering the markers and the false tooth model with a shaping agent to form a positioning stent; putting the positioning stent on the teeth in a mouth to perform tomography imaging to acquire a slice image of the preset slice plane; mounting a positioning aid having a positioning hole in the positioning stent according to the slice image pasted up on the tooth mold to guide an initial drill. A dental positioning stent for tomography imaging, and a manufacturing method, a using method, and components thereof are provided.

10 Claims, 23 Drawing Sheets

(56) References Cited

U.S. PATENT DOCUMENTS

| | | | |
|---|---|---|---|
| 5,967,777 A * | 10/1999 | Klein et al. | 433/75 |
| 7,086,860 B2 * | 8/2006 | Schuman et al. | 433/75 |
| 7,731,497 B2 * | 6/2010 | De Moyer | 433/72 |
| 2004/0219476 A1 | 11/2004 | Dadi | |
| 2006/0210949 A1 | 9/2006 | Stoop | |
| 2008/0064005 A1 | 3/2008 | Meitner | |
| 2010/0129768 A1 * | 5/2010 | Isidori | 433/75 |
| 2010/0151411 A1 | 6/2010 | Suter et al. | |

FOREIGN PATENT DOCUMENTS

| | | |
|---|---|---|
| JP | 2003-245289 A | 9/2003 |
| JP | 2006141561 A | 6/2006 |
| JP | 3149000 | 2/2009 |
| JP | 2009-531098 A | 9/2009 |
| TW | I244915 B | 12/2005 |
| WO | 2007079775 A1 | 7/2007 |
| WO | 2009066935 A1 | 5/2009 |

* cited by examiner

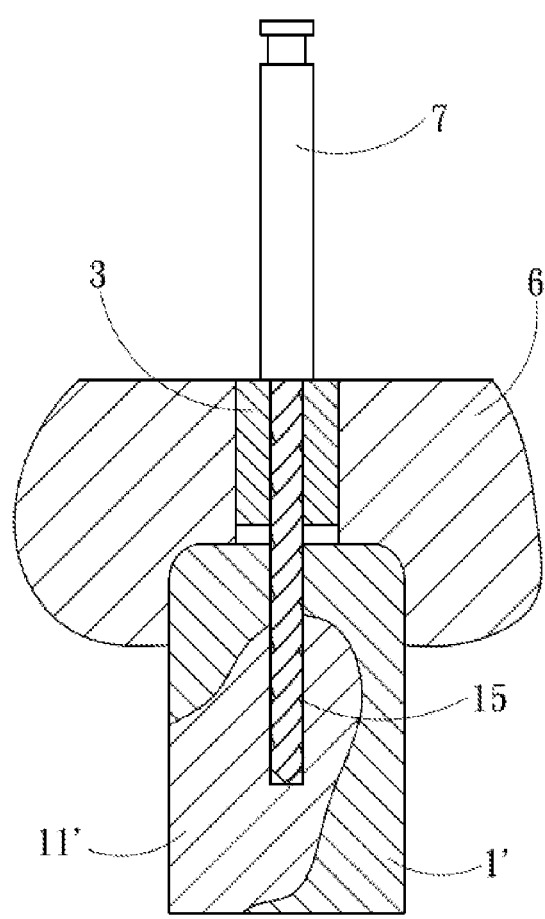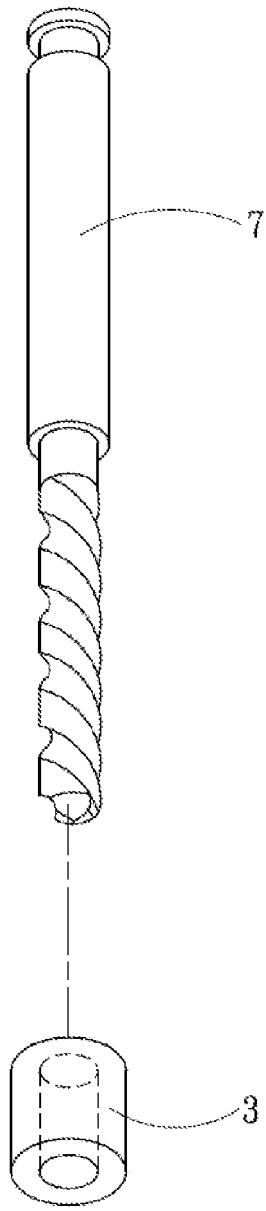
FIG. 8A
FIG. 8B

DENTAL POSITIONING STENT, AND MANUFACTURING METHOD, USING METHOD AND COMPONENTS FOR THE SAME

CROSS-REFERENCES TO RELATED APPLICATIONS

This non-provisional application claims priority under 35 U.S.C. §119(a) on Patent Application No. 99140979 filed in Taiwan, R.O.C. on 2010 Nov. 26, the entire contents of which are hereby incorporated by reference.

BACKGROUND

1. Technical Field

The disclosure relates to a dental positioning stent, and a manufacturing method, a using method, and components for the same, and more particularly to a dental positioning stent for positioning an implant and to take tooth tomography scanning slice images, and a manufacturing method, a using method, and components for the same.

2. Related Art

Before performing tooth implant surgery, a dentist normally makes a tooth mold according to the teeth of a patient, and determines a tooth implant position, and an implant angle and an implant depth of an implant on the tooth mold according to experiences. However, for patients, tooth structures are all different, and growth directions of teeth are slightly different. If only personal experiences are relied on, and no reliable aiding tools are available, an error may be incurred to an implant position, thereby harming neighboring teeth or nerves.

Tooth implant surgery therefore requires the aid of tomography scanning, so as to determine patient information such as a tooth structure and a depth of an alveolar bone, thereby evaluating selection of an implant and consideration of an implant position. However, a dentist can only speculate a slice plane position of an image on the tooth mold according to the tomography image, so as to judge the size of an implant to be used, an implant position, and an implant angle. In fact, errors may still occur, thereby incurring risks of harming neighboring teeth or nerves.

Please refer to FIG. 1, FIG. 1 is a schematic view of a ROC patent No. 1244915. The patent provides a method for making a tooth implant positioning guide hole using a tooth mold. First, a tooth mold a1 is coated with a silica gel, and the tooth mold a1 covers teeth of a patient to make a guide seat a2. By acquiring geometric data of a three-dimensional (3D) digital model of the teeth of the patient, a depth, a position, and an angle of drill required by tooth implant are analyzed with a computer, according to which a guide hole a21 is drilled, and a sleeve a22 is placed in the guide hole a21. Thus, a drill bit a3 guided by the sleeve a22 drills an implant hole in an alveolar bone.

However, the tooth implant position is analyzed through a computer, the analysis of which is difficult for the dentist to transform into a physical tooth mold, and is likely to result in error when in a tooth implant position of the guide seat a2 is transformed. In addition, the 3D image analysis software and the guide seat machining table are typically too costly to implement. More importantly, tooth implant evaluation cannot be performed according to a shape of a false tooth expected to be mounted and a gum image at the same time, and the tooth implant position and a tooth implant angle can only be analyzed according to the gum image, which may cause the implant to be inconsistent with adjacent teeth.

SUMMARY

Accordingly, a major objective of embodiments of the disclosure is to provide a dental positioning stent and a manufacturing method for the same, so as to aid tooth implant positioning, and help a dentist to evaluate tooth implant surgery accurately according to a tomography image and a tooth mold.

Another objective of the embodiments of the disclosure is to provide a dental positioning stent and a manufacturing method for the same, to take a tooth tomography scanning slice image and aiding a dentist to acquire an accurate slice image.

Another objective of the embodiments of the disclosure is to provide components used in a dental positioning stent for manufacturing a dental positioning stent and aiding tooth implant surgery.

An embodiment of the disclosure provides a dental positioning stent and a manufacturing method for the same, for positioning an implant to mount a false tooth on the implant. The manufacturing method includes the following steps: manufacturing a tooth mold according to teeth in a mouth of a patient, selecting a preset implant position of an implant on the tooth mold, and disposing a false tooth model in equal proportion to a false tooth on the tooth mold; selecting a preset slice plane passing through the preset implant position, and slicing the tooth mold and the false tooth model along the preset slice plane; fixing two markers in the preset slice plane on two sides of the tooth mold and the false tooth model respectively, where the markers are not penetrated by an X-ray; covering the markers, the false tooth model, and a part of the tooth mold surrounding the markers and the false tooth model with a shaping agent to form a positioning stent, where the shaping agent includes a resin polymer and a developer; putting the positioning stent on the teeth in the mouth to perform tomography imaging, so as to acquire a slice image of the preset slice plane; pasting up the slice image on a slice plane of the tooth mold in equal proportion; selecting a diameter, a length, an implant depth, and an implant angle of the implant according to the slice image pasted up on the tooth mold and a profile of the false tooth model; and mounting a positioning aid having a positioning hole in a corresponding position of the positioning stent to the implant, where when the positioning stent is placed in the mouth of the patient, a slider slides into the positioning hole to guide a drill.

An embodiment of the disclosure provides a dental positioning stent and a manufacturing method for the same, to take a tooth tomography scanning slice image. The manufacturing method includes the following steps: manufacturing a tooth mold according to teeth in a mouth, where the tooth mold includes a dental crown portion and a gum portion; selecting a preset slice plane of the tooth mold; fixing two markers in the preset slice plane on two sides of the tooth mold, where the markers are not penetrated by an X-ray; and covering the markers and a part of the tooth mold surrounding the markers with a shaping agent to form a positioning stent, where the shaping agent includes a resin polymer and a developer.

An embodiment of the disclosure provides components used in a dental positioning stent, for using with a drill, which include: a positioning aid, mounted in a positioning stent, where a center of the positioning aid has a positioning hole running through the positioning aid; a slider, sliding into the positioning hole to guide a drill.

An embodiment of the disclosure provides components used in a dental positioning stent, which include: a positioning aid, mounted in a positioning stent, where a center of the positioning aid has a positioning hole running through the positioning aid; a drill, including a cutting portion and a shank portion; and a slider, sliding into the positioning hole to guide a drill, where the sum of the heights of the slider and the positioning aid is essentially greater than or equal to the length of the cutting portion of the drill.

An embodiment of the disclosure provides components used in a dental positioning stent, for reaming the upper end of a guide hole, which include: a guide drill, including a cutting portion, a shank portion connected to the cutting portion and a cylindrical portion extending from the top of the cutting portion, and the top of the cutting portion is flat, such that after the cylindrical portion is placed in advance into the guide hole, the cutting portion reams the upper end of the guide hole.

Another objective of the embodiments of the disclosure is to provide a using method of a dental positioning stent, so as to aid manufacturing of an abutment tooth. A shape of the positioning stent corresponds to a tooth mold, and the positioning stent has a false tooth space corresponding to a shape of a false tooth. The method includes the following steps: mounting an analog implant in an implant hole of the tooth mold; putting the positioning stent on the tooth mold; and removing a part of the tooth mold according to boundaries of the false tooth space and the tooth mold and an upper end periphery of the analog implant to form a concave, so as to manufacture the abutment tooth according to the concave and the false tooth space.

Preferred embodiments of the disclosure and effects thereof are described below with reference to the drawings.

BRIEF DESCRIPTION OF THE DRAWINGS

The disclosure will become more fully understood from the detailed description given herein below for illustration only, and thus not limitative of the disclosure, wherein:

FIG. 8A is a schematic view of an implant hole according to the first embodiment;

FIG. 8B is a schematic view of an initial drill according to the first embodiment;

DETAILED DESCRIPTION

Figure 1:
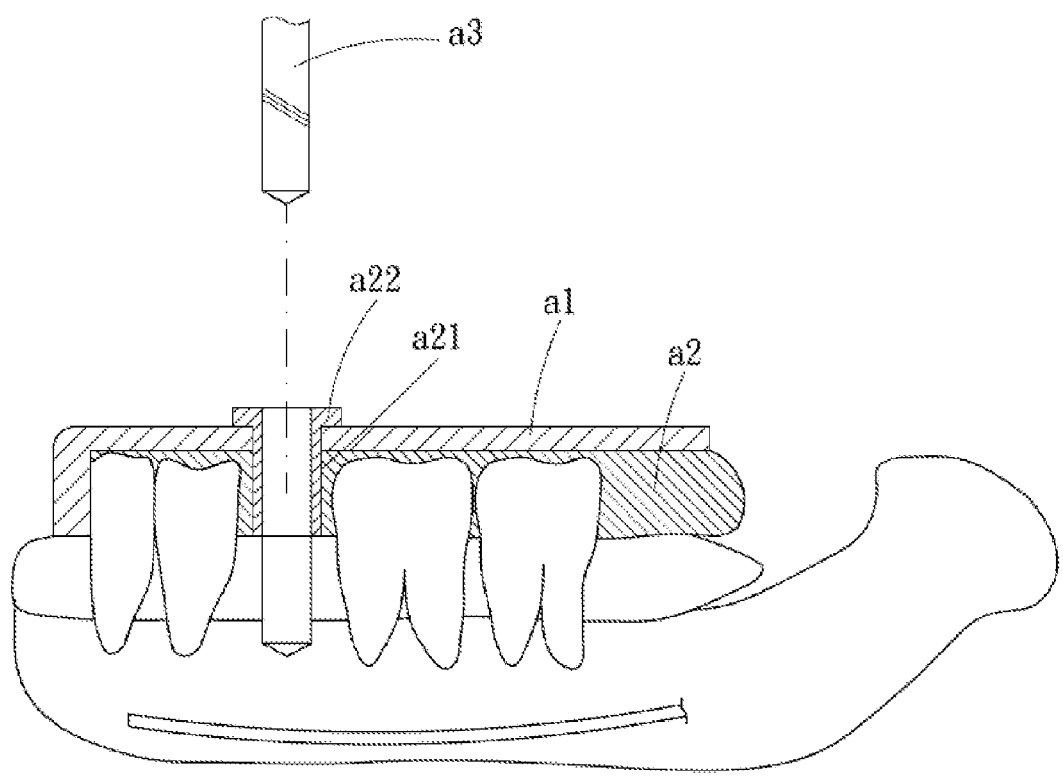
FIG. 1 is a schematic view of a dental positioning stent according to the prior art.
Figure 2:
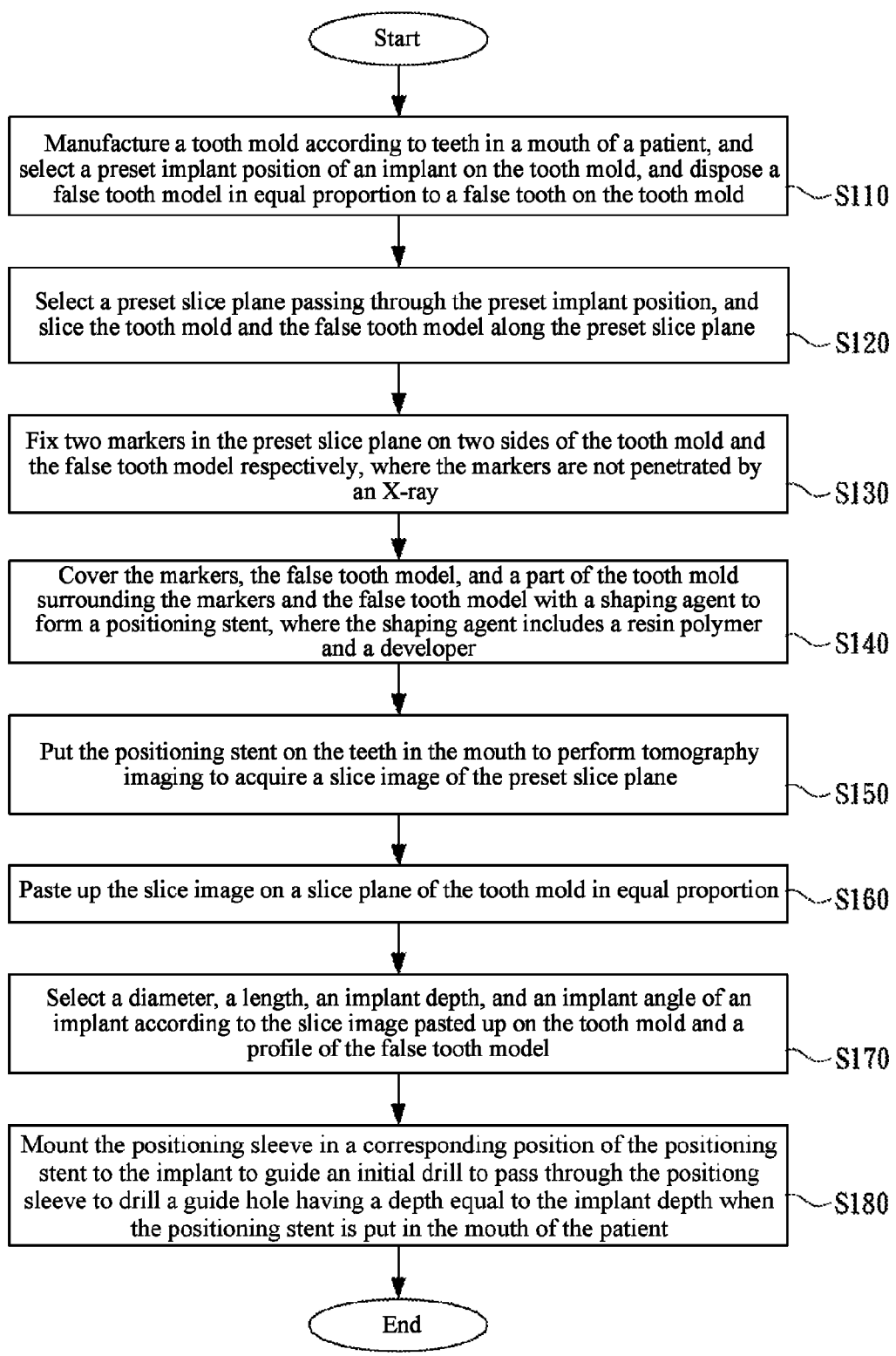
FIG. 2 is a flowchart according to a first embodiment.

Please refer to FIG. 2, is a flowchart according to a first embodiment. A dental positioning stent and a manufacturing method thereof provided by the disclosure are used for positioning an implant to mount a false tooth on the implant. The manufacturing method includes the following steps.

In Step S110, a tooth mold is manufactured according to teeth in a mouth of a patient, and a preset implant position of an implant on the tooth mold is selected, according to which a false tooth model in equal proportion to a false tooth is disposed on the tooth mold.

Figure 3:
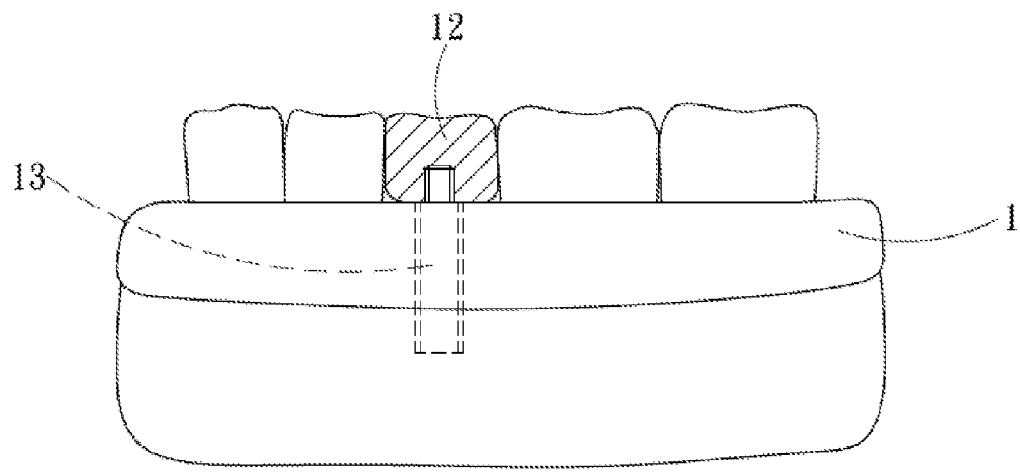
FIG. 3 is a model diagram according to the first embodiment.

Please refer to FIG. 3, is a model diagram according to the first embodiment. A tooth mold 1 is manufactured by rolling over according to teeth in a mouth of a patient, a false tooth model 12 in equal proportion to a false tooth expected to be mount is manufactured, and the false tooth model 12 is disposed on the tooth mold 1. A center of the false tooth model 12 is a preset implant position 13 of an implant.

Figure 4:
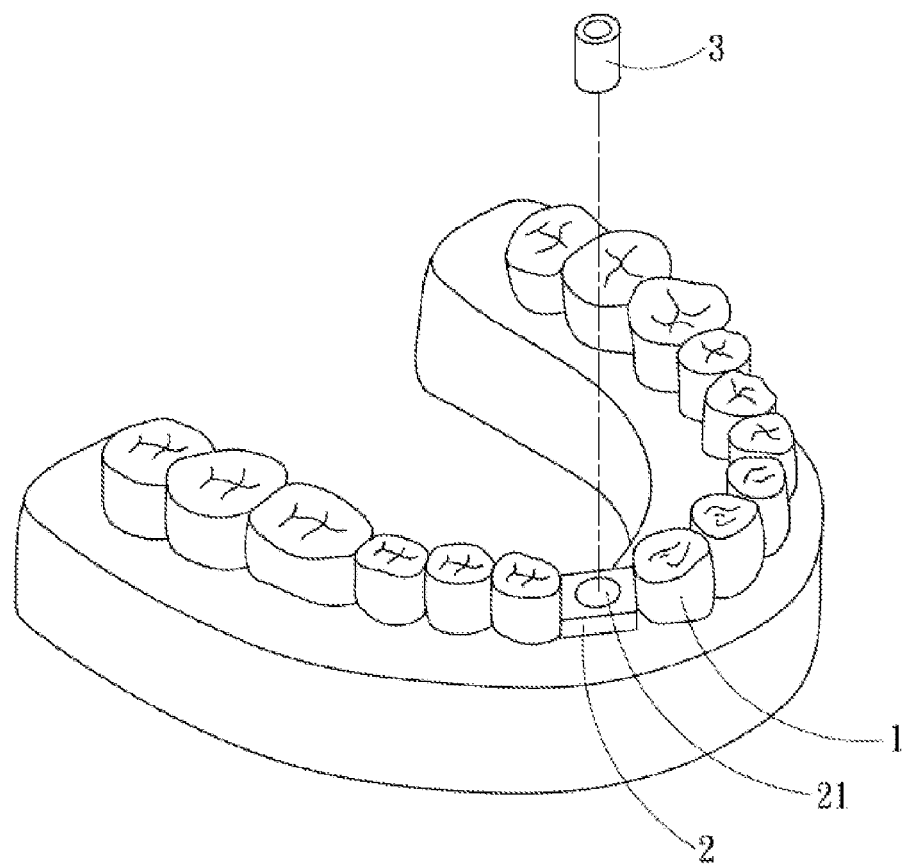
FIG. 4 is a schematic view of a preset implant position according to the first embodiment.

Please refer to FIG. 4, is a schematic view of a preset implant position according to the first embodiment. A step of selecting the preset implant position of the implant on the tooth mold 1 includes Step S111 and Step S112.

In Step S111, a positioning aid 2 on the tooth mold 1 is provided. An area of the tooth mold 1 covered by the positioning aid 2 is the same as that of the false tooth. A center of the positioning aid 2 has a positioning hole 21, and the positioning hole 21 runs through the positioning aid 2.

Here, the positioning aid 2 is used to estimate a mounting position and a space occupied by the false tooth. In some embodiment, the shape of the positioning aid 2 may be a square cuboid or a circle cuboid, but the disclosure is not limited thereto.

In Step S112, a positioning sleeve 3 is inserted into the positioning hole 21 of the positioning aid 2, and a preset implant position 13 is acquired in a center of the positioning sleeve 3.

Here, a diameter of the positioning hole 21 of the positioning aid 2 may be the same as that of the implant. A minimum distance between an outer edge of the positioning hole 21 and an outer edge of the positioning aid 2 is 1.5 mm, which is usually a thickness by which the false tooth covers the implant. A height of the positioning aid 2 may be 3 mm, which is usually a length by which the implant is exposed from a gum after tooth implanting. However, the diameter of the implant selected in the step is not thus determined, and may also be adjusted in subsequent steps. In particular, when a patient requires the mounting of consecutive false teeth, a plurality of positioning aids 2 is arranged to estimate mounting positions of the false teeth, which is both visually helpful and convenient.

In Step S120, a preset slice plane passing through the preset implant position 13 is selected, and the tooth mold 1 and the false tooth model 12 are sliced along the preset slice plane.

Figure 5:
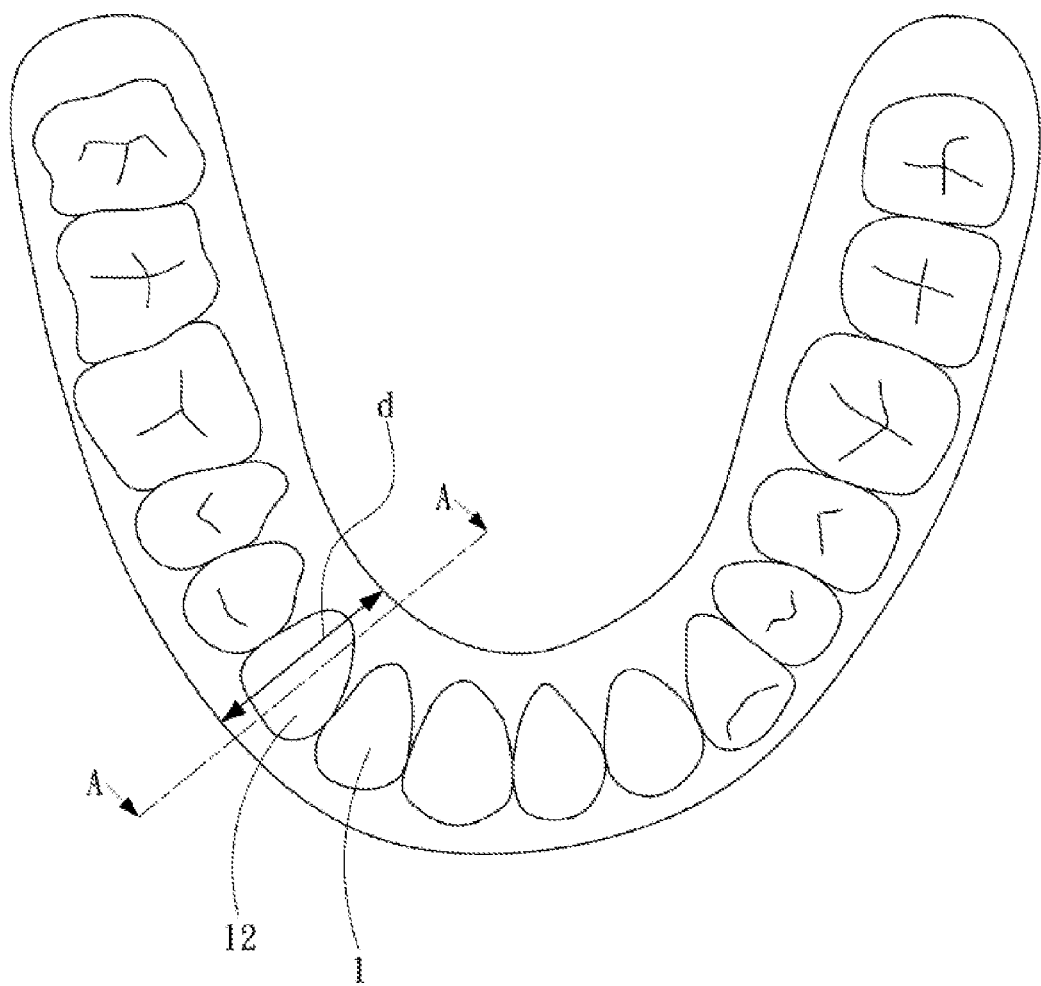
FIG. 5 is a schematic view of a preset slice plane according to the first embodiment.

Please refer to FIG. 5, a schematic view of a preset slice plane according to the first embodiment. A section along a line A-A is the preset slice plane, which usually passes through the preset implant position, is parallel to a vertical axis from a dental crown portion to a tooth root portion of an adjacent tooth, and is a section along a shortest distance d from a cheek side of the gum to a tongue side of the gum.

In Step S130, two markers 61 are fixed in the preset slice plane on two sides of the tooth mold 1 and the false tooth model 12 respectively. The markers 61 cannot be penetrated by an X-ray.

Figure 6A:
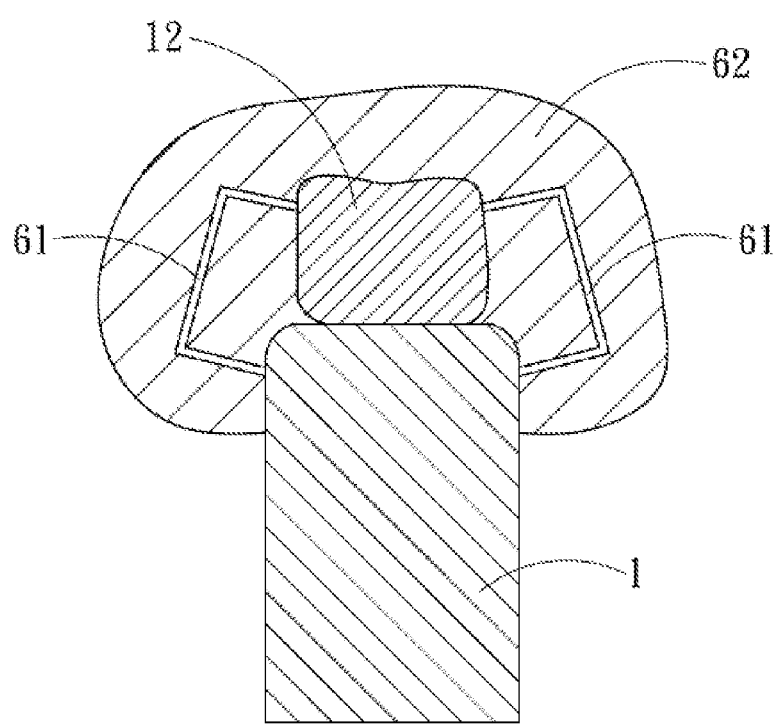
FIG. 6A is a sectional view of the preset slice plane according to the first embodiment.

Please refer to FIG. 6A, a sectional view of the preset slice plane according to the first embodiment. In some embodiment, the markers 61 may be U-shaped metal objects with openings opposite each other. One end of the marker 61 is connected to the false tooth model 12, and the other end of the marker 61 is connected to the tooth mold 1, but shapes of the markers 61 are not limited thereto. Thus, the preset slice plane is marked. Only when the two markers 61 are both included in one of the tomography images, can the tomography image be a tomography image of the preset slice plane.

However, the two markers 61 may also be replaced with a marking object, which is located anywhere in the preset slice plane. The marking object has a recognizable profile, for example a geometric profile, in the section of the preset slice plane. For example, the marking object may be formed by a triangle formed by a metal wire, and the marking object is placed in the preset slice plane along a plane defined by the triangle. Therefore, when a tomography image has a triangular pattern corresponding to the marking object, the slice image can be determined to be an expected image of the preset slice plane.

Figure 6B:
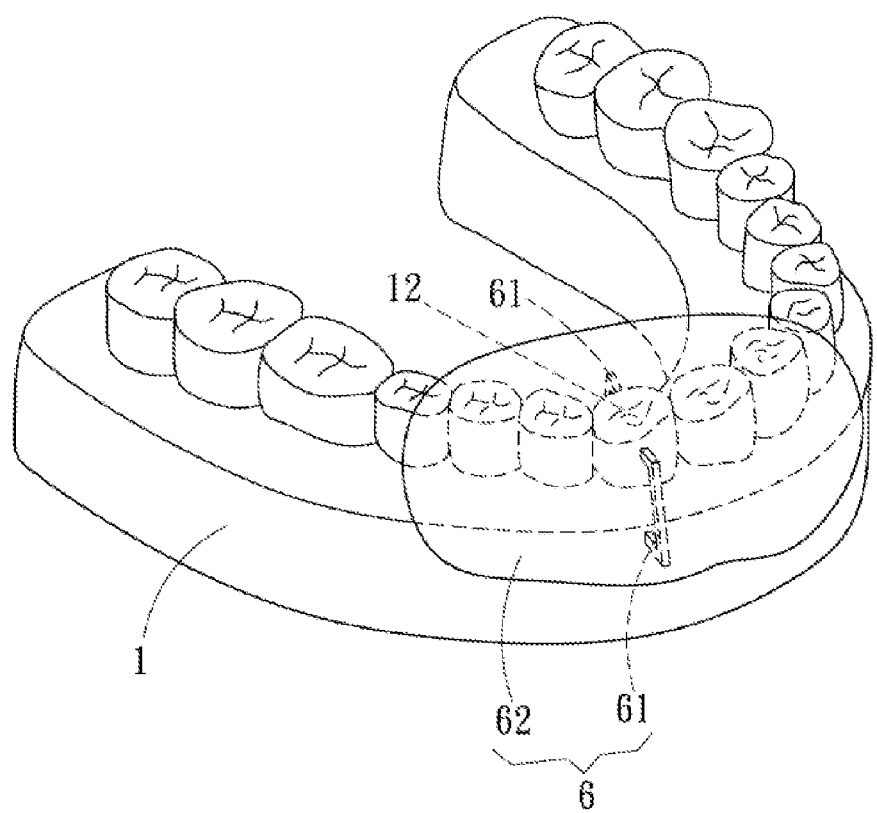
FIG. 6B is a schematic three-dimensional view of a positioning stent according to the first embodiment.

In Step S140, a shaping agent 62 is used to cover the markers 61, the false tooth model 12, and a part of the tooth mold 1 surrounding the markers 61 and the false tooth model 12, thereby forming a positioning stent 6. The shaping agent 62 includes a resin polymer and a developer. Please refer to FIG. 6B, a schematic three-dimensional view of a positioning stent 6 according to the first embodiment.

Here, the developer may be barium sulfate. Both the resin polymer and gum tissue can be penetrated by X-ray, so that the resin polymer and gum tissue are not shown in a tomography image. Therefore, the developer is mixed in the positioning stent 6, so as to identify boundaries between the positioning stent 6 and the gum tissue.

In Step S150, the positioning stent 6 is put on the teeth in the mouth to perform tomography imaging, so as to acquire a slice image of the preset slice plane.

Here, the positioning stent 6 manufactured in Step S140 is placed on the corresponding teeth of the patient to perform the tomography imaging, and the slice image of the preset slice plane can be acquired accurately through the two markers 61 disposed in Step S130.

Furthermore, if it is found that a slice image better than the preset slice plane exists by checking a tomography imaging result, a section corresponding to the better slice image may be sliced to replace the original preset slice plane.

In Step S160, the slice image is pasted up on a slice plane of the tooth mold 1 in equal proportion. Here, the slice image is cut along an edge of an image of the positioning stent 6 and the gum, and is pasted up on the slice plane of the tooth mold 1, thereby acquiring a tooth mold having the slice image.

Herein the step can enable a dentist to correctly check a section of the gum of a patient, which is more realistic compared with viewing a tomography image only through a computer, and the dentist is therefore able to evaluate more accurately a state of the patient, in order to decide how to perform tooth implant surgery.

In Step S170, a diameter, a length, an implant depth, and an implant angle of an implant 14 are selected according to the slice image pasted up on the tooth mold 1 and a profile of the false tooth model 12.

Figure 7:
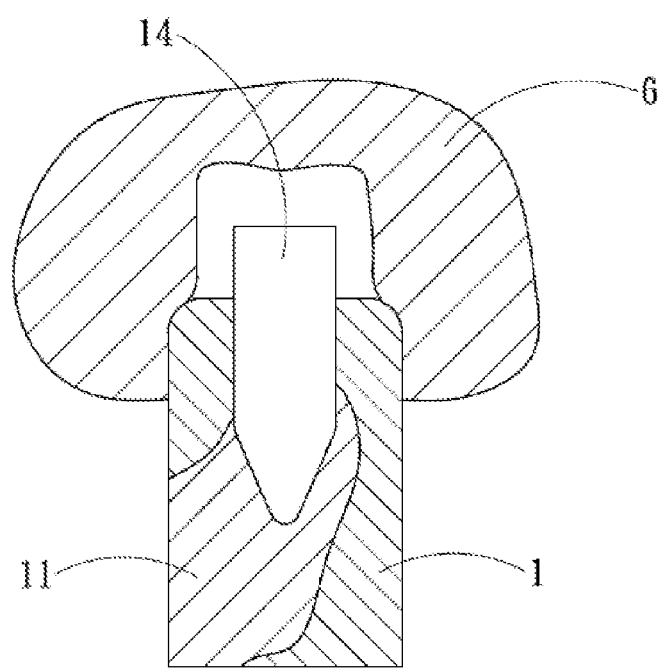
FIG. 7 is a schematic view of a selected implant according to the first embodiment.

Here, please refer to FIG. 7, a schematic view of a selected implant according to the first embodiment. The dentist can estimate a relative position of the implant 14 and the false tooth to be mounted according to a range of an alveolar bone 11 shown in the slice image and using a profile of the false tooth model 12 provided inside the positioning stent 6, so as to select the suitable diameter and length of the implant 14 and determine the implant angle and depth.

Before this step, a false tooth coat of the false tooth model 12 may otherwise be manufactured to replace the positioning stent 6 of this step, and the false tooth coat can be sliced according to the preset slice plane. Therefore, by means of this step, the tomography image of the gum and a shape of the false tooth to be mounted can be considered at the same time to decide the diameter, length, implant depth, and implant angle of the implant 14, thereby making consideration of the tooth implant more comprehensive and accurate.

In Step S180, the positioning sleeve 3 is mounted in a corresponding position of the positioning stent 6 to the implant 14. The positioning sleeve 3 guides an initial drill 7 to pass through the positioning sleeve 3 to drill a guide hole 15 having a depth equal to the implant depth in a gum 1' when the positioning stent 6 is placed in the mouth of a patient (as shown in FIG. 8A). Here, an alveolar bone 11' of the gum 1' corresponds to the alveolar bone 11 of the tomography image.

Please refer to FIG. 8A, a schematic view of the guide hole according to the first embodiment. The positioning sleeve 3 is in the shape of a hollow sleeve, and is mounted in the positioning stent 6, so that the initial drill 7 can pass through the positioning sleeve 3 to drill the guide hole 15 according to the preset implant position, implant angle, and implant depth. Please refer to FIG. 8B, a schematic view of the initial drill according to the first embodiment. Through the positioning sleeve 3, upon reaching a certain depth the initial drill 7 may be prevented from going downwards any further, thereby preventing the initial drill 7 from drilling a depth exceeding the expected depth. Here, a side surface of the positioning sleeve 3 is a non-smooth surface, on which a groove or a recessed point may be disposed (not shown), so that the positioning stent 6 can cover the positioning sleeve 3 tightly, thereby preventing the positioning sleeve 3 departing from the positioning stent 6 due to a force generated during drilling. Here, preferably, an upper end of the positioning stent 6 may substantially be aligned with an upper end of the positioning sleeve 3, so as not to block viewing of the dentist.

Thus, before the tooth implant surgery the dentist can put the positioning stent 6 manufactured in Steps S110 to S180 on corresponding teeth of the patient to drill the guide hole 15 having the expected position, angle, and depth for mounting the implant 14 and the false tooth. In addition, through the positioning sleeve 3, upon drilling to the expected depth the initial drill 7 may be prevented from going downwards any further, thereby preventing harming nerves or adjacent teeth of the patient.

Figure 9:
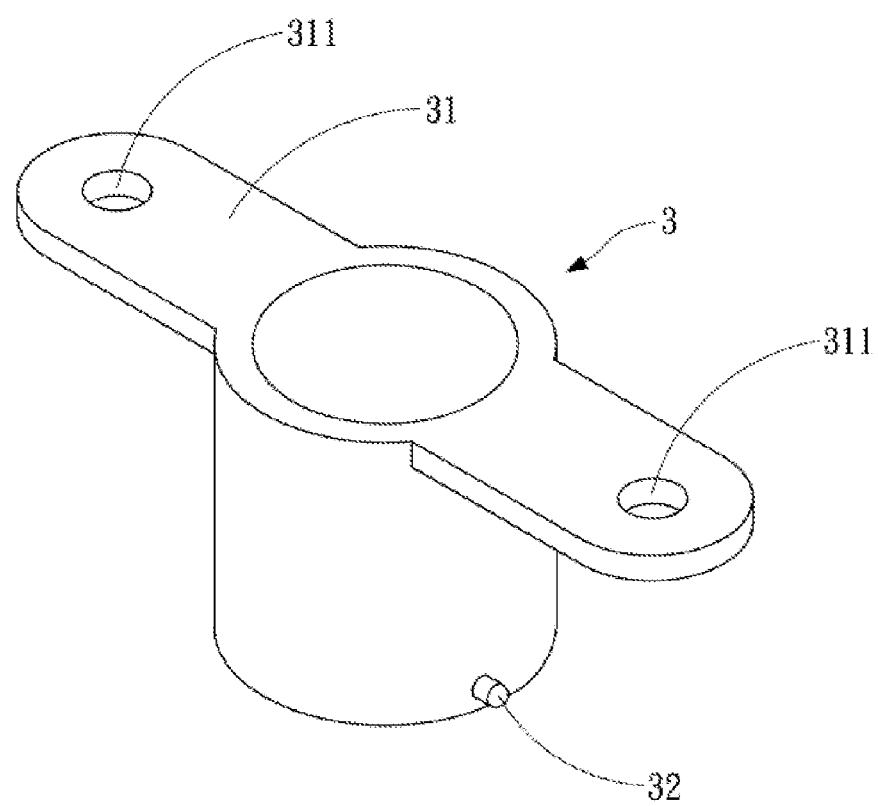
FIG. 9 is another schematic view of a positioning sleeve according to the first embodiment.

Please refer to FIG. 9, another schematic view of the positioning sleeve according to the first embodiment. The positioning sleeve 3 bears a downward force of the initial drill 7, and thus in order to prevent the positioning sleeve 3 departing from the positioning stent 6 due to the downward force, a flange portion 31 extending from the positioning sleeve 3 provides an upward support force. The flange portion 31 may in fact be two symmetrical extended wings, has a larger area relative to that of a main body of the positioning sleeve 3, and ends of the flange portion 31 are provided with holes 311. In addition, a distance may be kept between the flange portion 31 and the upper end of the positioning stent 6, so that the dentist can grip the positioning sleeve 3 after drilling the guide hole 15.

In addition, an outer surface of the positioning sleeve 3 is disposed with a protruding portion 32, so as to prevent the positioning sleeve 3 from rotating together with the initial drill 7. Alternatively, an outer shape of the positioning sleeve 3 may be changed into a polygonal prism, and a shape of the positioning hole 21 of the positioning aid 2 corresponds to the outer shape of the positioning sleeve 3, so as to prevent the positioning sleeve 3 from rotating. Here, the protruding portion 32 may be in the form of a protruding point.

Thus, after the initial drill 7 drills the guide hole 15, the dentist can further ream the guide hole 15 into an implant hole, so that a width of the implant hole is consistent with the diameter of the implant, which is conducive to the mounting of the implant.

Figure 10A:
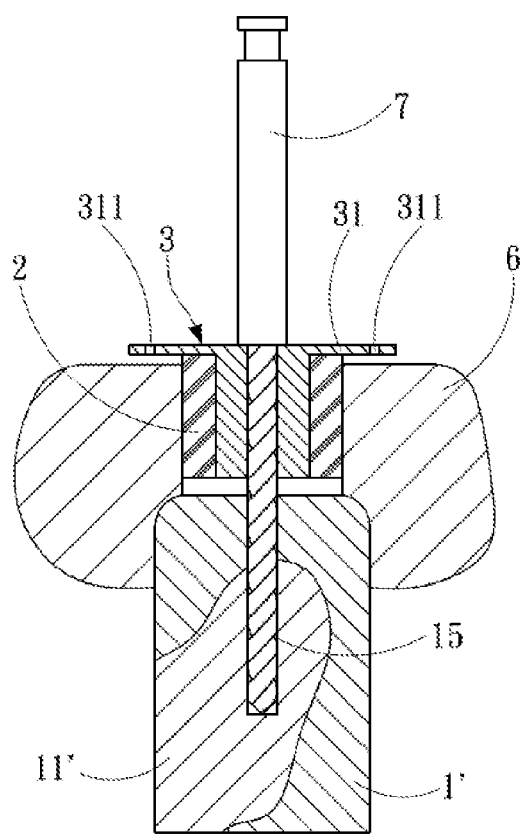
FIG. 10A is a schematic view of an implant hole according to a second embodiment.
Figure 10B:
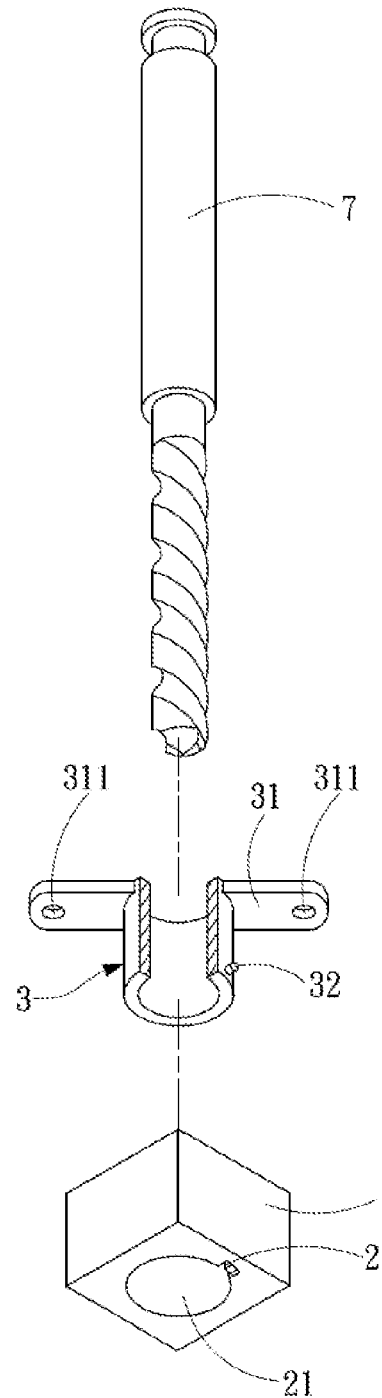
FIG. 10B is a schematic view of an initial drill according to the second embodiment.

Please refer to FIG. 10A and FIG. 10B. FIG. 10A is a schematic view of a guide hole according to a second embodiment, and FIG. 10B is a schematic view of an initial drill according to the second embodiment. Referring to the steps in the first embodiment, Step S180 in this embodiment further includes the following steps.

In Step S280, the positioning sleeve 3 and the positioning aid 2 are mounted in the positioning stent 6, and the positioning sleeve 3 is placed in the positioning hole 21 of the positioning aid 2.

Here, the positioning sleeve 3 is used to guide the initial drill 7 to drill the guide hole 15. The positioning sleeve 3 may be of the structure shown in FIG. 9 and have the flange portion 31 and the protruding portion 32, or the outer shape of the positioning sleeve 3 may be a polygonal prism. The positioning sleeve 3 is placed in the positioning hole of the positioning aid 2, and the flange portion 31 presses against an upper end of the positioning aid 2. After the initial drill 7 drills downwards to a depth, a shank portion of the initial drill 7 presses against the positioning sleeve 3 and stops going downwards. By adjusting heights of the positioning aid 2 and the positioning sleeve 3, the guide hole 15 of the expected depth can be drilled. An inner wall of the positioning aid 2 also has a groove 22 corresponding to the protruding portion 32 to engage with the positioning sleeve 3, thereby preventing the positioning sleeve 3 from rotating. Furthermore, an end of the groove 22 extends laterally, so that after being placed into the positioning aid 2 the positioning sleeve 3 rotates to lock the protruding portion 32, which prevents the positioning sleeve 3 from sliding out when tooth implant is performed on an upper row of teeth.

In addition, an outside of the positioning aid 2 also has a structure like the flange portion 31 of the positioning sleeve 3 (not shown), or a side surface of the positioning aid 2 is disposed with a groove (not shown), so as to prevent the positioning aid 2 departing from the positioning stent 6 due to the force generated during the drilling.

Here, a long pole having calibrations and a screw hole may be used to simulate the depth, angle, and position of the guide hole 15 drilled by the initial drill 7. Through the protruding portion 32 and the groove 22, the positioning sleeve 3 can be fixed in the positioning hole 21 of the positioning aid 2. The positioning sleeve 3 is fixed on the long pole temporarily by gluing. Thus, heights of the positioning aid 2 and the positioning sleeve 3 relative to the guide hole 15 are fixed. Then, the positioning aid 2 and the positioning sleeve 3 are mounted in the positioning stent 6, and the long pole is taken out. In fact, a hole may be drilled in the positioning stent 6, and after the positioning stent 6 having the hole sleeves the long pole, the positioning aid 2 and the positioning sleeve 3, the shaping agent 62 is used to fill the hole.

Figures 11A, 11B:
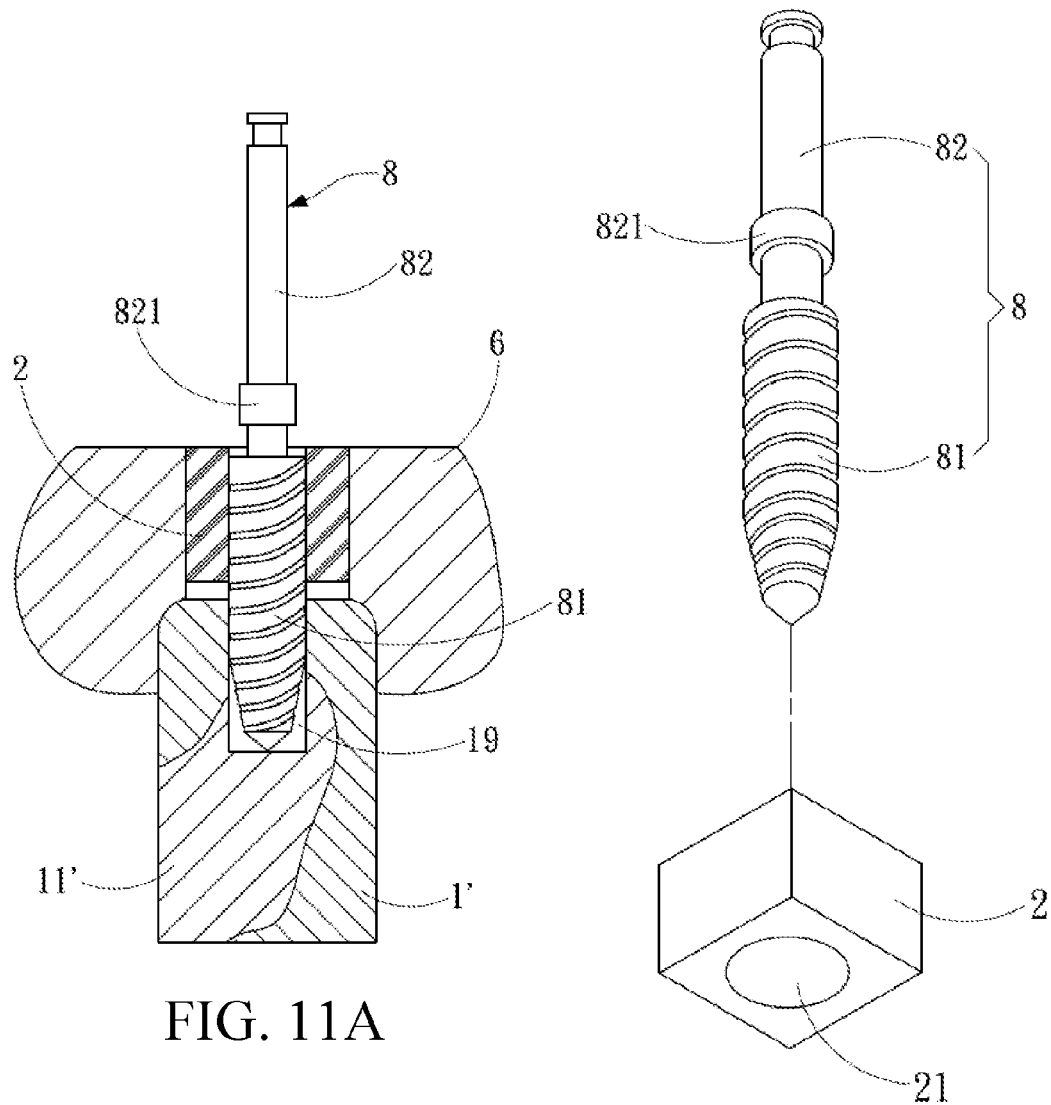
FIG. 11A is a schematic view of reaming according to the second embodiment.
FIG. 11B is a schematic view of an enlargement drill according to the second embodiment.

Please refer to FIG. 11A and FIG. 11B. FIG. 11A is a schematic view of the reaming according to the second embodiment, and FIG. 11B is a schematic view of an enlargement drill according to the second embodiment. After Step S280, the method further includes the following steps.

In Step S281, the positioning sleeve 3 is removed to allow an enlargement drill 8 to pass through the positioning hole 21 of the positioning aid 2. The enlargement drill 8 includes a cutting portion 81 and a shank portion 82, and the cutting portion 81 reams the guide hole 15.

Here, the enlargement drill 8 passes through the positioning hole 21 to precisely ream the guide hole 15 drilled by the initial drill 7. In addition, a diameter of the cutting portion 81 can be increased step by step using different enlargement drills 8, so as to ream the guide hole 15 step by step to form an implant hole 19.

Figure 12:
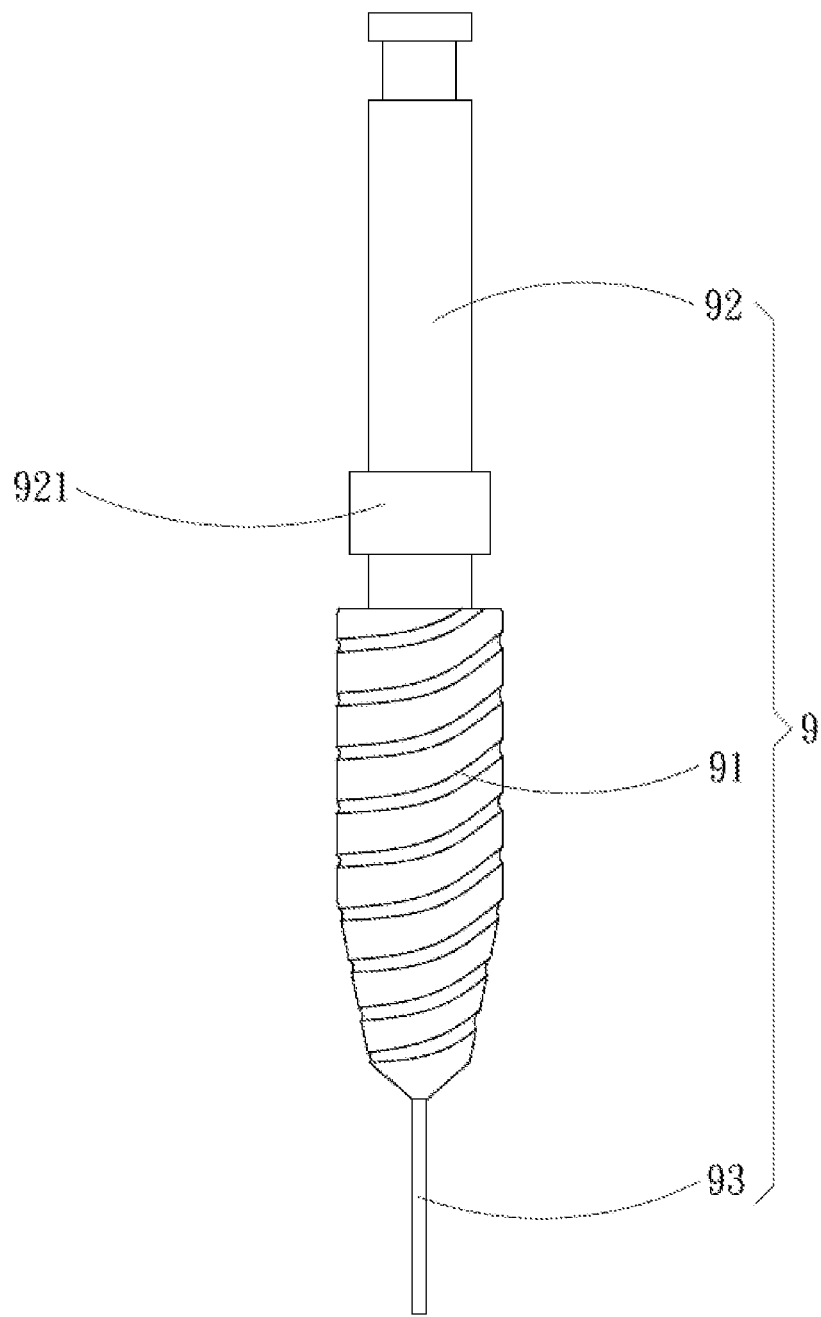
FIG. 12 is a schematic view of a guide drill according to the second embodiment and a third embodiment.

Please refer to FIG. 12. FIG. 12 is a schematic view of a guide drill according to the second embodiment. Before using the enlargement drill 8, a guide drill 9 may be used to ream an upper end of the guide hole 15. The guide drill 9 is like the enlargement drill 8 to have a cutting portion 91 and a shank portion 92, and have a cylindrical portion 93 extending from a top of the cutting portion 91. A top of the cylindrical portion 93 is flat. Thus, after the cylindrical portion 93 is placed in advance into the guide hole 15 drilled in Step S180, the cutting portion 91 reams downwards the upper end of the guide hole 15.

Then, the enlargement drill 8 is used to continue to perform reaming downwards according to a part reamed by the guide drill 9, so as to ream the guide hole 15 more steady and more accurately to form the implant hole 19.

Figures 13A, 13B:
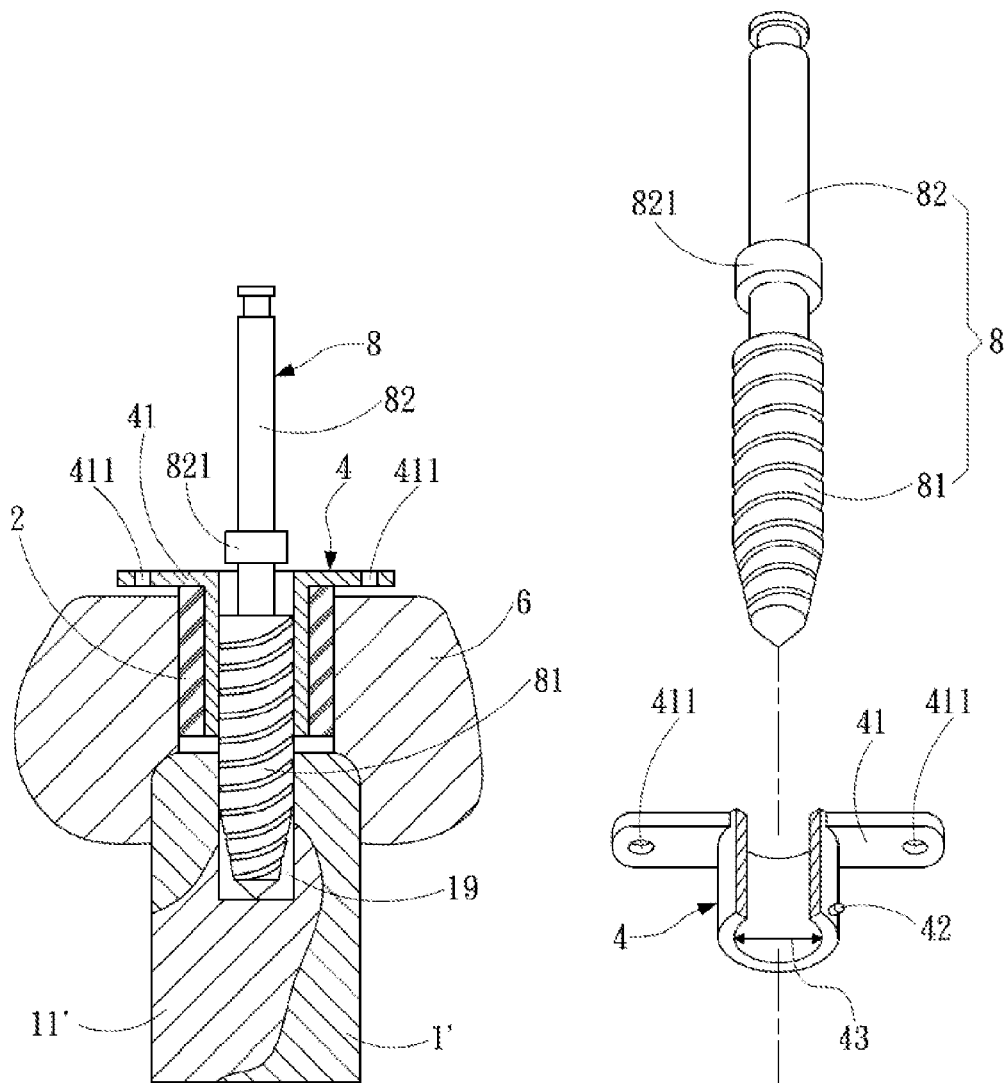
FIG. 13A is a schematic view of reaming according to the third embodiment.
FIG. 13B is a schematic view of an enlargement drill according to the third embodiment.

Please refer to FIG. 13A and FIG. 13B. FIG. 13A is a schematic view of reaming according to a third embodiment, and FIG. 13B is a schematic view of an enlargement drill according to the third embodiment. After the guide hole 15 is achieved by the method of the second embodiment, the guide hole 15 may also be reamed using the positioning aid 2 together with a reaming sleeve 4 of the embodiment. After Step S280, the method further includes the following steps.

In Step S381, the positioning sleeve 3 is removed. Here, after the positioning sleeve 3 is removed, the positioning aid 2 remains in the positioning stent 6.

In Step S382, the reaming sleeve 4 is placed in the positioning hole 21 of the positioning aid 2 to guide the enlargement drill 8. The enlargement drill 8 includes the cutting portion 81 and the shank portion 82, and the cutting portion 81 reams the guide hole 15 to form the implant hole 19. For an enlargement drill 8 having a cutting portion 81 of a different diameter, a reaming sleeve 4 of a different diameter 43 can be used for replacement.

Here, in fact a structure of the reaming sleeve 4 also may have a flange portion 41, holes 411 in the flange portion 41, and a protruding portion 42. A difference between the structure of reaming sleeve 4 and that of the positioning sleeve 3 lies in a value of the diameter 43. The reaming sleeve 4 should allow the enlargement drill 8 to pass through, so that the diameter 43 is consistent with the diameter of the cutting portion 81 of the enlargement drill 8. For the enlargement drill 8 having the cutting portion 81 of a different diameter, the reaming sleeve 4 of a different diameter 43 can also be provided.

An advantage of using the reaming sleeve 4 to aid the reaming lies in that reaming sleeves 4 of different diameters 43 can be used for replacement to meet requirements of reaming in ascending order. However, in Step S281 of the second embodiment, the positioning aid 2 of the positioning stent 6 should be taken out before using a positioning aid 2 having the positioning hole 21 of a different diameter for replacement.

Figures 14A, 14B:
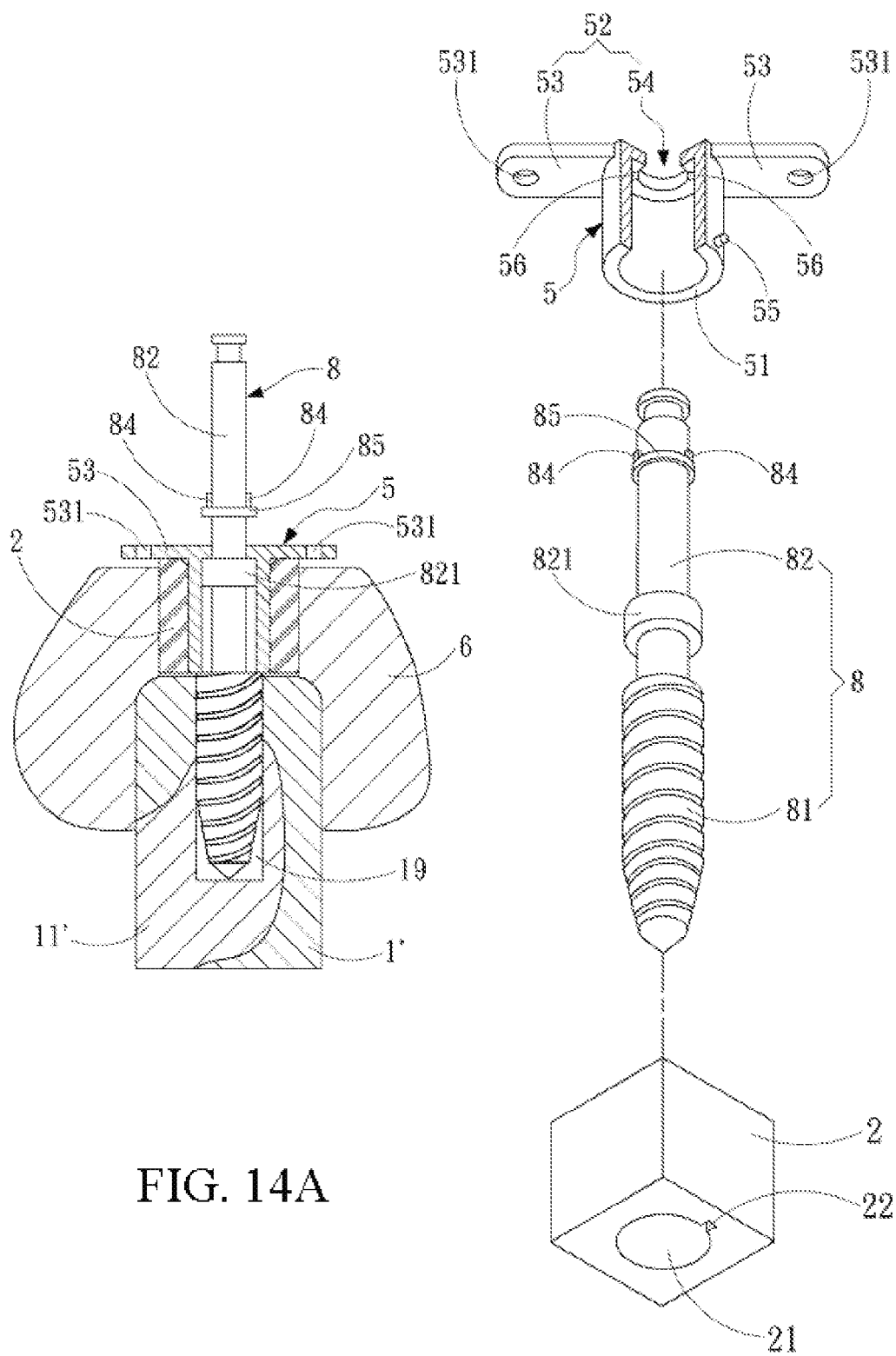
FIG. 14A is a schematic view of reaming according to a fourth embodiment.
FIG. 14B is a schematic view of enlargement drill according to the fourth embodiment.

Please refer to FIG. 14A and FIG. 14B. FIG. 14A is a schematic view of reaming according to a fourth embodiment, and FIG. 14B is a schematic view of an enlargement drill according to the fourth embodiment. After the guide hole 15 is achieved by the method of the second embodiment, the guide hole 15 may also be reamed using the positioning aid 2 together with a positioning cap 5 of the embodiment. After Step S280, the method further includes the following steps.

In Step S481, the positioning sleeve 3 is removed. Here, after the positioning sleeve 3 is removed, the positioning aid 2 remains in the positioning stent 6.

In Step S482, a positioning cap 5 is provided, and the positioning cap 5 slides into the positioning hole 21 of the positioning aid 2, so as to guide the enlargement drill 8 to ream the guide hole 15 to form the implant hole 19.

Here, the positioning cap 5 includes a tube portion 51 and a flat portion 52. The flat portion 52 covers one end of the tube portion 51 and extends outwards to form a flange portion 53. In some embodiments, the flange portion 53 may be two symmetrical extended wings, and holes 531 are opened at ends of the wings, so as to be gripped by the dentist. A center of the flat portion 52 has a drill bit guide hole 54 running through the flat portion 52. The tube portion 51 is used to receive the enlargement drill 8. Additionally, if the flat portion 52 is thick enough to stabilize the drill 8, the positioning cap 5 is suitable for different sizes of diameter of the enlargement drill 8. The enlargement drill 8 includes the cutting portion 81 and the shank portion 82. The shank portion 82 passes through the drill bit guide hole 54, and the cutting portion 81 reams the guide hole 15. The shank portion 82 of the enlargement drill 8 is disposed with a plurality of positioning elements 84 protruding from a surface of the shank portion 82. In addition, the flat portion 52 of the positioning cap 5 has recessed holes 56 corresponding to the positioning elements 84. The recessed holes 56 may be larger than the positioning elements 84, so that the enlargement drill 8 can pass through the positioning cap 5. An elastic ring 85 is put around a surface of the enlargement drill 8, and is fixed below the positioning elements 84. After the enlargement drill 8 drills downwards to make the elastic ring 85 contact with the positioning cap 5, the enlargement drill 8 stops reaming, thereby avoiding drilling the implant hole 19 exceeding the expected depth.

In fact, the elastic ring 85 may be a rubber ring, and the number of the elastic ring 85 may be increased or an elastic ring 85 of a different width may be selected as required, thereby adjusting the expected drilling depth flexibly. Here, the positioning elements 84 can prevent the elastic ring 85 from moving upwards.

For the same reason, the enlargement drill 8 shown in FIG. 11A of the second embodiment and FIG. 13A of the third embodiment may also include the positioning elements 84 and the elastic ring 85, thereby ensuring the implant hole 19 having the expected depth to be drilled. Here, a diameter of the elastic ring 85 shall be larger than the diameter of the implant hole 19.

Figures 14C, 14D:
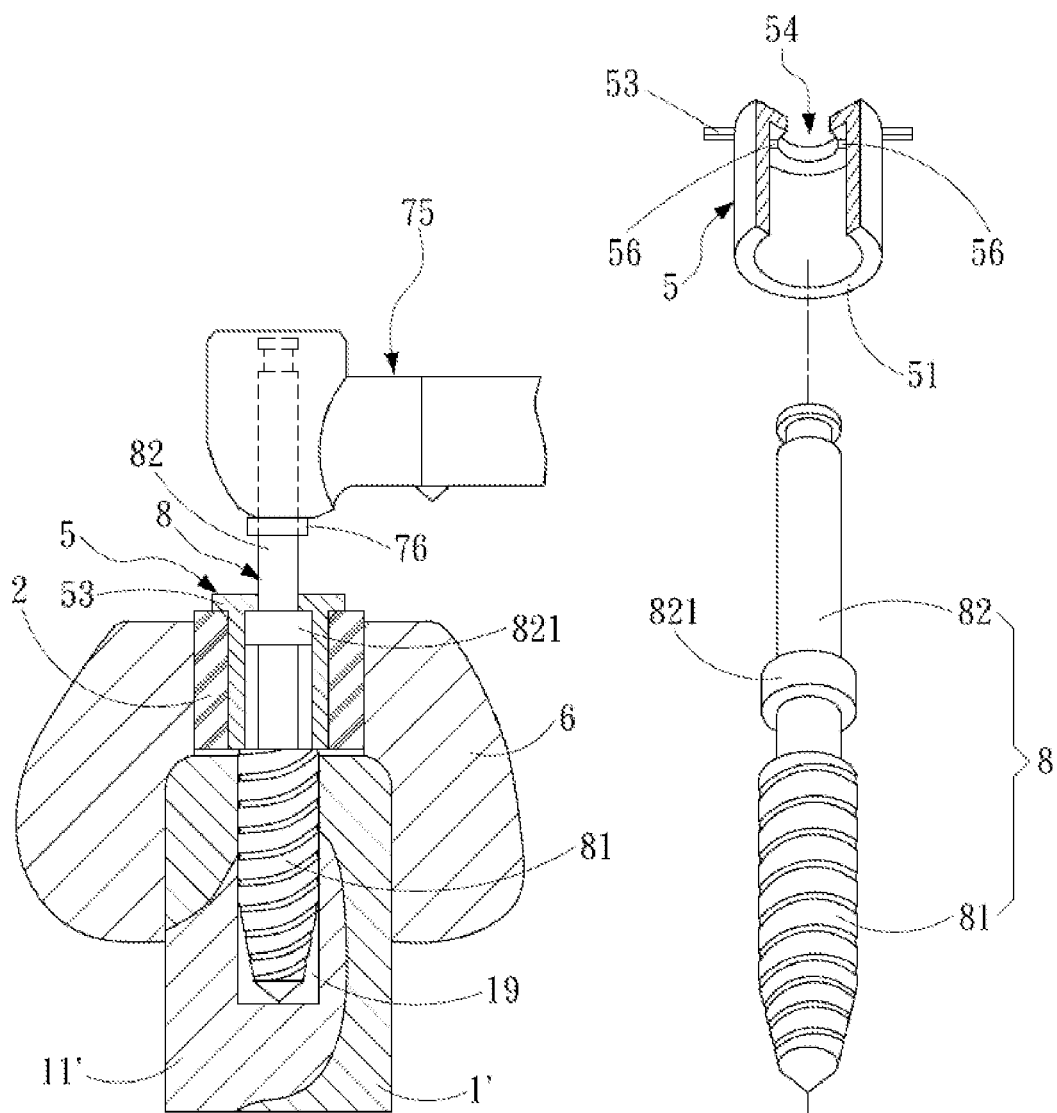
FIG. 14C is a schematic view of another reaming according to the fourth embodiment.
FIG. 14D is a schematic view of another positioning aid, another enlargement drill and another positioning cap according to the fourth embodiment.

Here, the disposition of the positioning elements 84, the elastic ring 85, and the recessed holes 56 are only exemplary, and the expected drilling depth may also be set in other manners in the first, second, third, and fourth embodiments. For example, as shown in FIG. 14C, at a connecting location of a tooth implant machine hand-piece 75 and the enlargement drill 8, the initial drill 7, or other drill bit, at least one sleeve 76 of a specific height may surround the drill bit to replace the positioning elements 84 and the elastic ring 85. When the tooth implant machine hand-piece 75 goes downwards to make a front end of the sleeve 76 press against the positioning cap 5, the drill bit is prevented from going downwards any further. So, when using the sleeve 76 in FIG. 13A of the third embodiment, the front end of the sleeve 76 presses against the reaming sleeve 4. Similarly, when using the sleeve 76 in FIG. 11A of the second embodiment, the front end of the sleeve 76 presses against the positioning aid 2. When using the sleeve 76 in FIG. 8A of the first embodiment, the front end of the sleeve 76 presses against positioning sleeve 3.

A diameter of the drill bit guide hole 54 of the positioning cap 5 is consistent with a diameter of the shank portion 82 of the enlargement drill 8. In some embodiments, the shank portion 82 further includes a shank head portion 821. A diameter of the shank head portion 821 is larger than that of the shank portion 82, and the shank head portion 821 engages with an inner wall of the tube portion 51, so that a drilling direction of the enlargement drill 8 can be stabled. The positioning cap 5 is applicable to various enlargement drills 8 having the cutting portions 81 of different diameters, since although the diameters of the cutting portions 81 of the enlargement drills 8 are different the diameters of the shank head portions 821 of the enlargement drill 8 are the same. In some embodiments, the enlargement drill 8 does not have the shank head portion 821, and the shank portion 82 is directly connected to the cutting portion 81. Accordingly, when the shank portion 82 passes through the positioning cap 5, a part of the cutting portion 81 is in the tube portion 51. There are different sizes of the enlargement drill 8 can be used when the diameter of cutting portion 81 is smaller than the caliber of the tube portion 51.

Figure 14E:
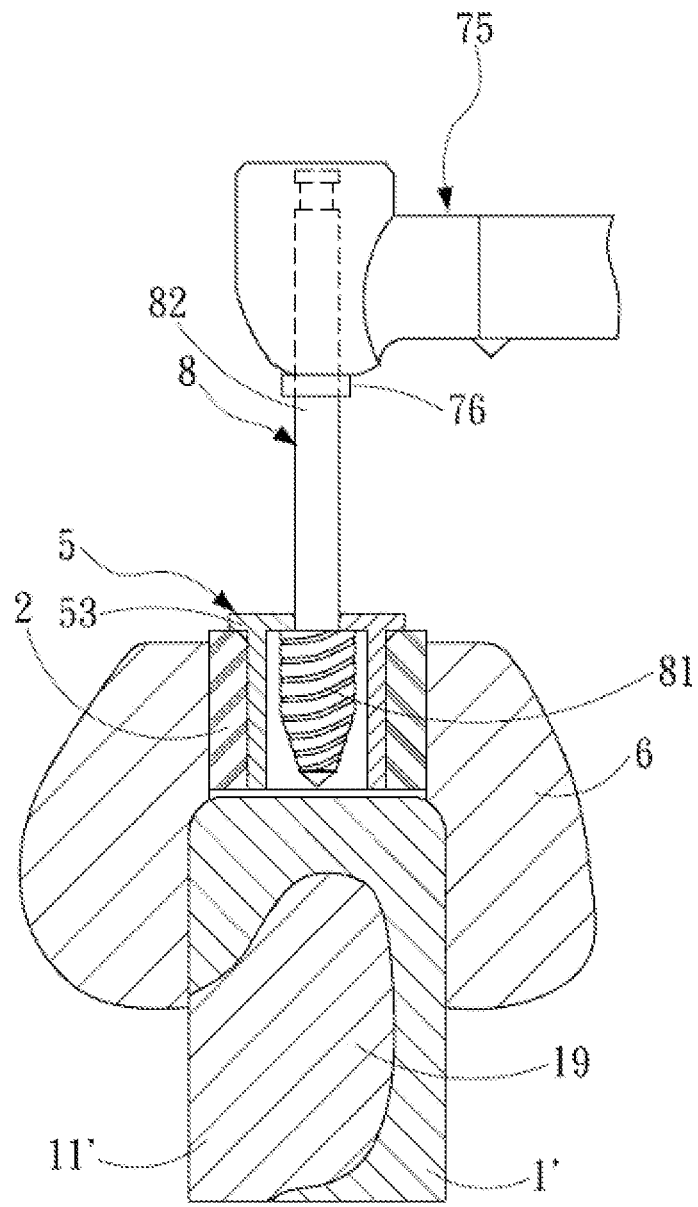
FIG. 14E is a schematic view of another aspect of the reaming according to the forth embodiment.

Furthermore, referring to FIG. 14E, which a schematic view of another aspect of the reaming according to the forth embodiment. The sum of the heights of the positioning aid 2 and the positioning cap 5 is essentially greater than or equal to the length of the cutting portion of the initial drill 7, the length of that of the enlargement drill 8 or the length of the cutting portion of the guide drill 9. Alternatively, the height of the positioning aid 2 or the positioning cap 5 is greater than or equal to the length of the cutting portion of the initial drill 7, the length of that of the enlargement drill 8 or the length of the cutting portion of the guide drill 9. For example, the length of the cutting portion 81 in FIG. 14E is shorter than the length of the cutting portion 81 in FIG. 14C. Referring to FIG. 14E, the whole of the cutting portion 81 is in the positioning cap 5. Accordingly, before sliding the positioning cap 5 into the positioning hole 21, the positioning aid 2, the positioning cap 5 and the cutting portion 81 in FIG. 14E occupy less space than that in FIG. 14C. Furthermore, using the enlargement drill 8 in FIG. 14E brings less heat than using the enlargement drill 8 in FIG. 14C.

Here, an outer shape of the positioning aid 2 or the positioning cap 5 may be polygonal or round. When the outer shape of the positioning cap 5 is round, a side surface of the positioning cap 5 is disposed with a protruding portion 55. A wall of the positioning hole 21 of the positioning aid 2 also has the groove 22 corresponding to the protruding portion 55, so that the positioning aid 2 engages with the positioning cap 5 to prevent the positioning cap 5 from rotating. Alternatively, when the outer shape of the positioning cap 5 is polygonal, the wall of the positioning hole 21 of the positioning aid 2 also has a corresponding shape to prevent the positioning cap 5 from rotating together with the enlargement drill 8.

In some embodiments, the flange portion 53 may be in the form of two protruding points shown in FIG. 14C and FIG. 14D. FIG. 14C is a schematic view of another reaming according to the fourth embodiment, and FIG. 14D is a schematic view of another positioning aid, another enlargement drill and another positioning cap according to the fourth embodiment. It can be realized that the shape of the positioning aid 2 may be a circle cuboid. The flange portion 53 shown in FIG. 14D are smaller than the flange portion 53 shown in FIG. 14B. Please referring to FIG. 14C and FIG. 14D and comparing to FIG. 14A and FIG. 14B, the positioning aid 2 does not have the groove 22, the positioning cap 5 does not have the protruding portion 55, and the enlargement drill 8 does not have the positioning elements 84 and the elastic ring 85. In some embodiments, the flange portion 53 may be in the form of ring (not shown).

Figure 14F:
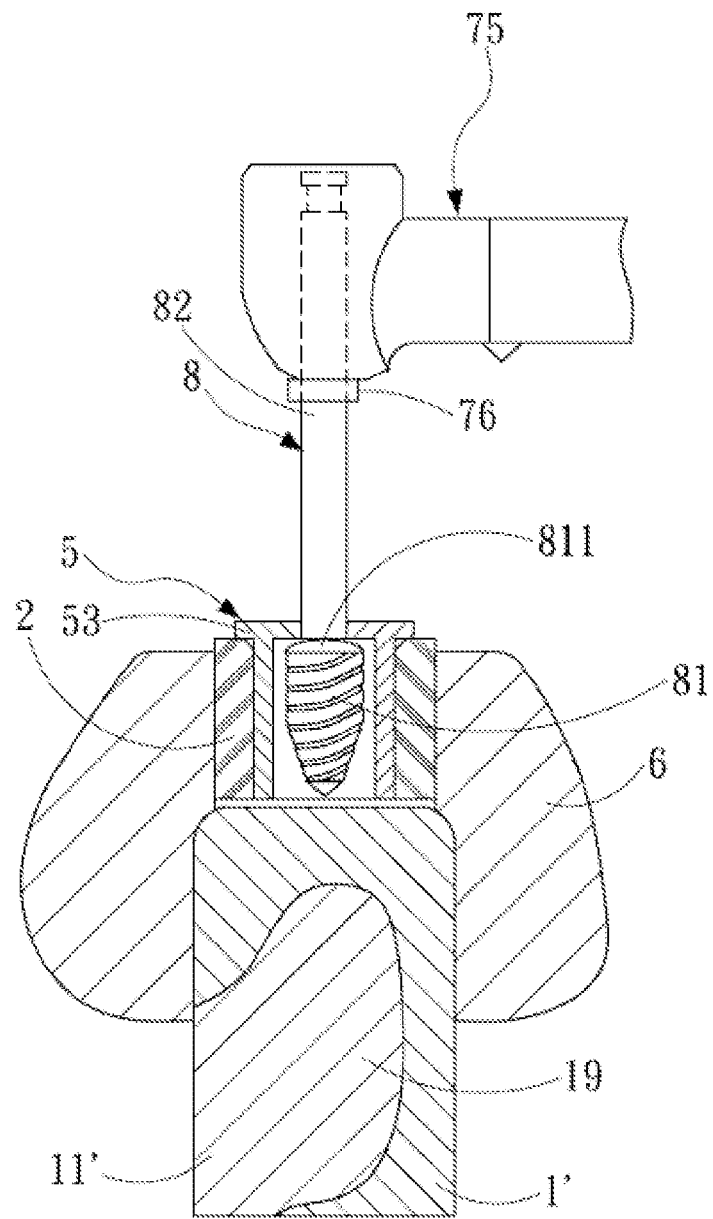
FIG. 14F is a schematic view of the other aspect of the reaming according to the forth embodiment.

Please refer to FIG. 14F. FIG. 14F is a schematic view of the other aspect of the reaming according to the forth embodiment. Comparing FIG. 14E and the FIG. 14F, FIG. 14F further has a shield 811 which is disposed on the cutting portion 81. In some embodiments, the shield 811 is circular and includes a concave side, a convex side opposite to the concave side and a hole for passing through the shank portion 82. The concave side faces the cutting portion 81. The shield 811 is used to prevent the cutting portion 81 from damaging the positioning cap 5. Additionally, a receiving space is formed between the shield 811 and the cutting portion 81 to collect bone chips when drilling. In one embodiment, the shield 811 extends a prop to be against the cutting portion 81 for preventing the shield 811 from being cut by the cutting portion 81. In one embodiment, the cutting portion 81 extends a prop to be against the shield 811 for preventing the shield 811 from being cut by the cutting portion 81. Here, the shield 811 also can be used for the guide drill 9 to be disposed on the cutting portion 91 of the guide drill 9.

Please refer to FIG. 12. FIG. 12 is a schematic view of the guide drill according to the third embodiment. Before using the enlargement drill 8, the guide drill 9 may be used to pass through the positioning hole 21 of the positioning aid 2 to ream the upper end of the guide hole 15. The guide drill 9 has the cutting portion 91 and the shank portion 92 the same as those of the enlargement drill 8, and has the cylindrical portion 93 extending from the top of the cutting portion 91. The top of the cylindrical portion 93 is flat. Thus, after the cylindrical portion 93 is placed in advance into the guide hole 15 drilled in Step S180, the cutting portion 91 reams downwards the upper end of the guide hole 15. Here, as in the manner in which the enlargement drill 8 cooperates with the positioning cap 5, a shank head portion 921 of the guide drill 9 is placed in the tube portion 51 of the positioning cap 5.

Next, the enlargement drill 8 is used to continue to perform reaming downwards according to the part reamed by the guide drill 9, so as to ream the guide hole 15 more steadily and more accurately to form the implant hole 19.

Figures 15A, 15B:
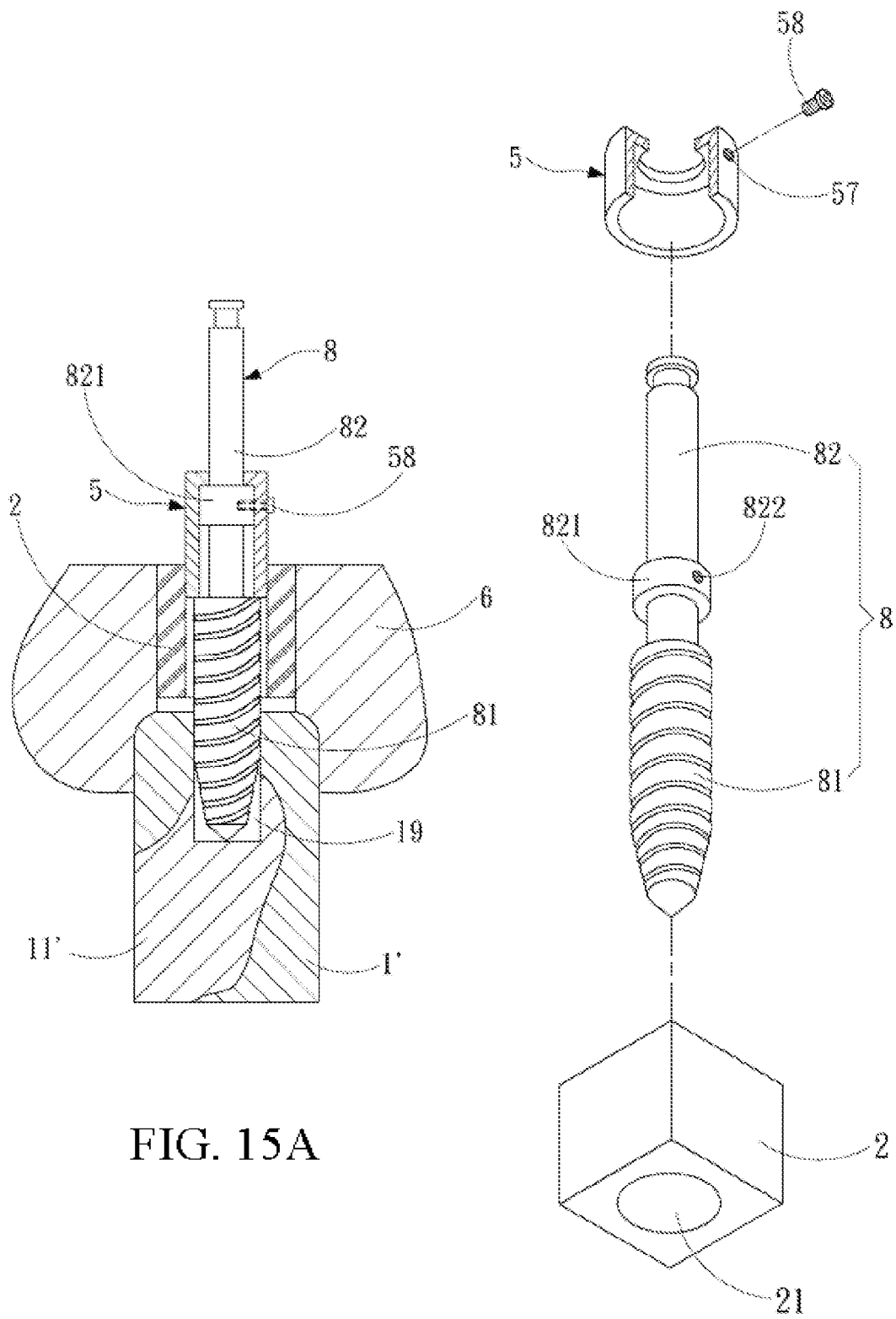
FIG. 15A is a schematic view of another aspect of a positioning cap according to the fourth embodiment.
FIG. 15B is a schematic view of another aspect of a positioning cap according to the fourth embodiment.

In some embodiments, the guide drill 9 does not have the shank head portion 921, and the shank portion 92 is directly connected to the cutting portion 91. Accordingly, when the shank portion 92 passes through the positioning cap 5, a part of the cutting portion 91 is in the tube portion 51. In some embodiment, please refer to FIG. 15A and FIG. 15B, schematic views of another aspect of the positioning cap according to the fourth embodiment. The positioning cap 5 includes a screw hole 57 disposed at an upper end of the positioning cap 5, so that a screw 58 passes through the screw hole 57, and is connected to a screw hole 822 of the enlargement drill 8, thereby fixing the positioning cap 5 on the enlargement drill 8. In addition, the screw 58 protrudes from an outside of the positioning cap 5 to exert the function of the flange portion 53. Additionally, the screw hole 822 may be at any location on the enlargement drill 8, and is not limited to be at the shank head portion 821.

Here, the initial drill 7 in FIG. 10A does not have the shank head portion. In some embodiments, the initial drill 7 have the shank head portion like the enlargement drill 8 or the guide drill 9.

Here, the positioning cap 5 may not have the flange portion 53 or the protruding portion 55 shown in FIG. 14A and FIG. 14B, and the inner wall of the positioning aid 2 is not required to have the groove 22 corresponding to the protruding portion 55 either. In addition, the positioning cap 5 is fixed on the enlargement drill 8, and the screw 58 provides a function of a drilling stopping point, so that no additional positioning element 84 is required to be disposed on the enlargement drill 8.

The above-mentioned positioning sleeve 3, the above-mentioned reaming sleeve 4 and the above-mentioned positioning cap 5 belong to sliders, each of which having a guiding hole. In other words, the sliders include but not limited to the positioning sleeve 3, the reaming sleeve 4 and the positioning cap 5. In addition, the above-mentioned initial drill 7, the above-mentioned enlargement drill 8 and the above-mentioned guide drill 9 belong to drills. In other words, the drills include but not limited to the initial drill 7, the enlargement drill 8 and the guide drill 9. The drill also can be a trephine bur.

In view of the above, the tooth implant surgery can be completed precisely. After the tooth implant surgery, the implanted tooth of the patient can be molded after the surgery for comparison with the positioning stent 6 to evaluate whether the expectation of the surgery is met.

Figure 16:
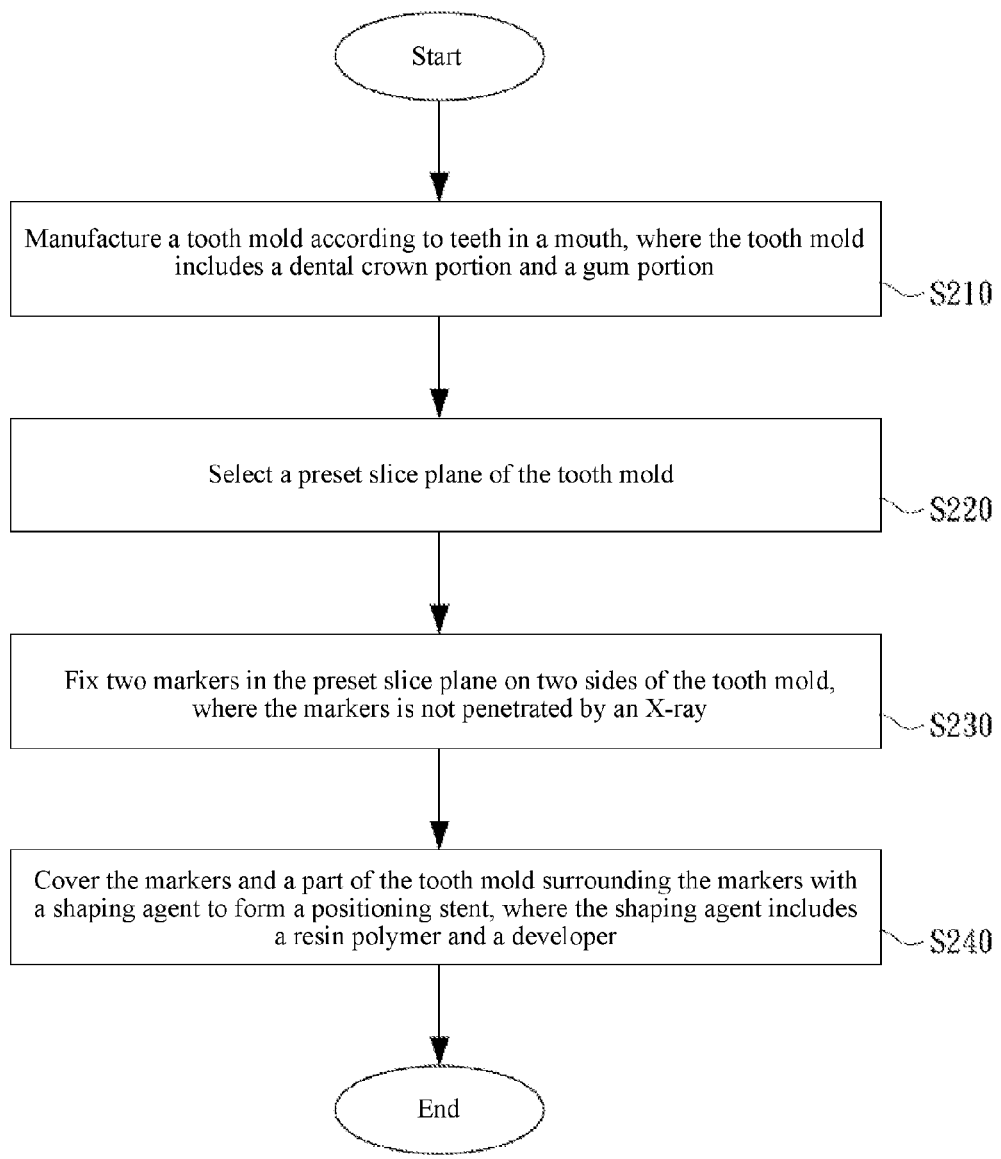
FIG. 16 is a flowchart according to a fifth embodiment.

Please refer to FIG. 16, a flowchart according to a fifth embodiment. The disclosure provides a dental positioning stent and a manufacturing method thereof to take a tooth tomography scanning slice image, and the manufacturing method includes the following steps.

In Step S210, a tooth mold 1 is manufactured according to teeth in a mouth. The tooth mold 1 includes a dental crown portion 16 and a gum portion 17. Here, in the first embodiment, the tooth mold 1 is manufactured according to teeth of the patient to which the false tooth is mounted, but this embodiment is not limited thereto, and is applicable to any demand to take a tomography image of a specific section.

In Step S220, a preset slice plane of the tooth mold 1 is selected. Here, a slice plane of a specific slice image to be acquired is selected.

In Step S230, two markers 61 are fixed in the preset slice plane on two sides of the tooth mold 1. The markers 61 cannot be penetrated by an X-ray.

Figure 17:
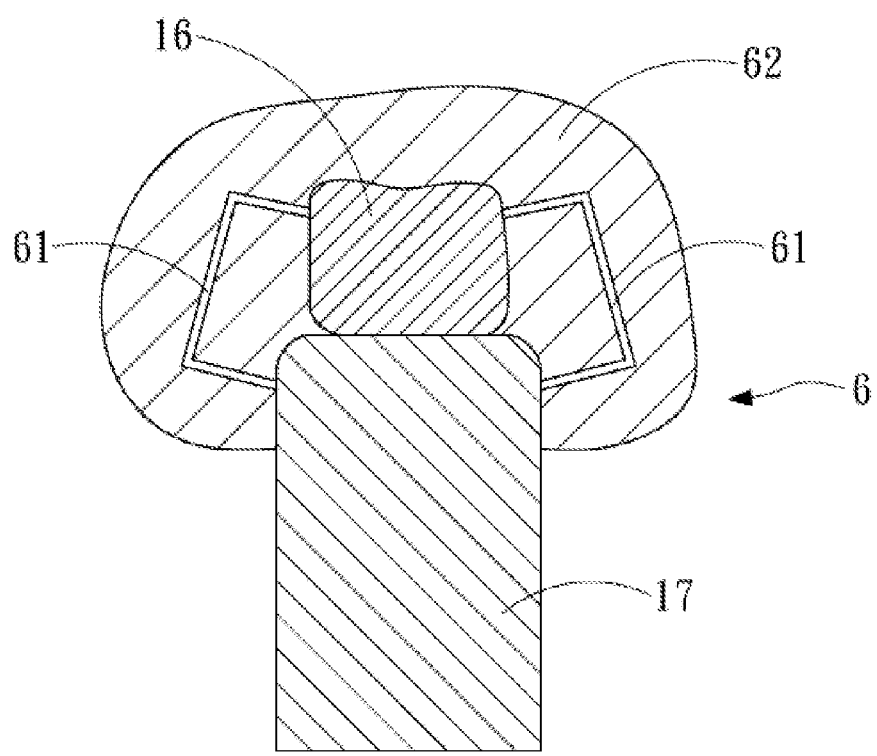
FIG. 17 is a sectional view of a preset slice plane according to the fifth embodiment.

Here, please refer to FIG. 17, FIG. 17 is a sectional view of the preset slice plane according to the fifth embodiment. The markers 61 may be U-shaped metal objects with openings opposite each other. One end of the marker 61 is connected to the dental crown portion 16 of the tooth mold 1, and the other end of the marker 61 is connected to the gum portion 17 of the tooth mold 1, but shapes of the markers 61 are not limited thereto. Thus, the preset slice plane is marked. Only when the two markers 61 are both included in a tomography image, can the tomography image be a tomography image of the preset slice plane.

However, the two markers 61 may also be, as stated in the first embodiment, replaced by a marking object, which is located on one side of the tooth mold 1 and the false tooth model 12, and the marking object has a recognizable profile, for example a geometric profile, in the section of the preset slice plane.

In Step S240, a shaping agent 62 is used to cover the markers 61 and a part of the tooth mold 1 surrounding the markers 61, thereby forming a positioning stent 6. The shaping agent 62 includes a resin polymer and a developer.

Here, the developer may be barium sulfate. Both the resin polymer and gum tissue can be penetrated by X-ray, so that the resin polymer and gum tissue are not shown in a tomography image. Therefore, the developer is mixed in the positioning stent 6, so as to identify boundaries between the positioning stent 6 and the gum tissue. Before Step S240, the method further includes: coating a separating agent around the preset slice plane of the tooth mold 1. After Step S240, the method may further include: after the shaping agent 62 is cured, taking the positioning stent 6 off the tooth mold 1.

Thus, for a patient, when the tooth tomography scanning is performed, the positioning stent 6 is placed in the mouth of the patient.

With the aforementioned steps, a dentist can mark the tooth slice plane on the tomography image, so as to make the slice image more accurate and reliable.

Figure 18:
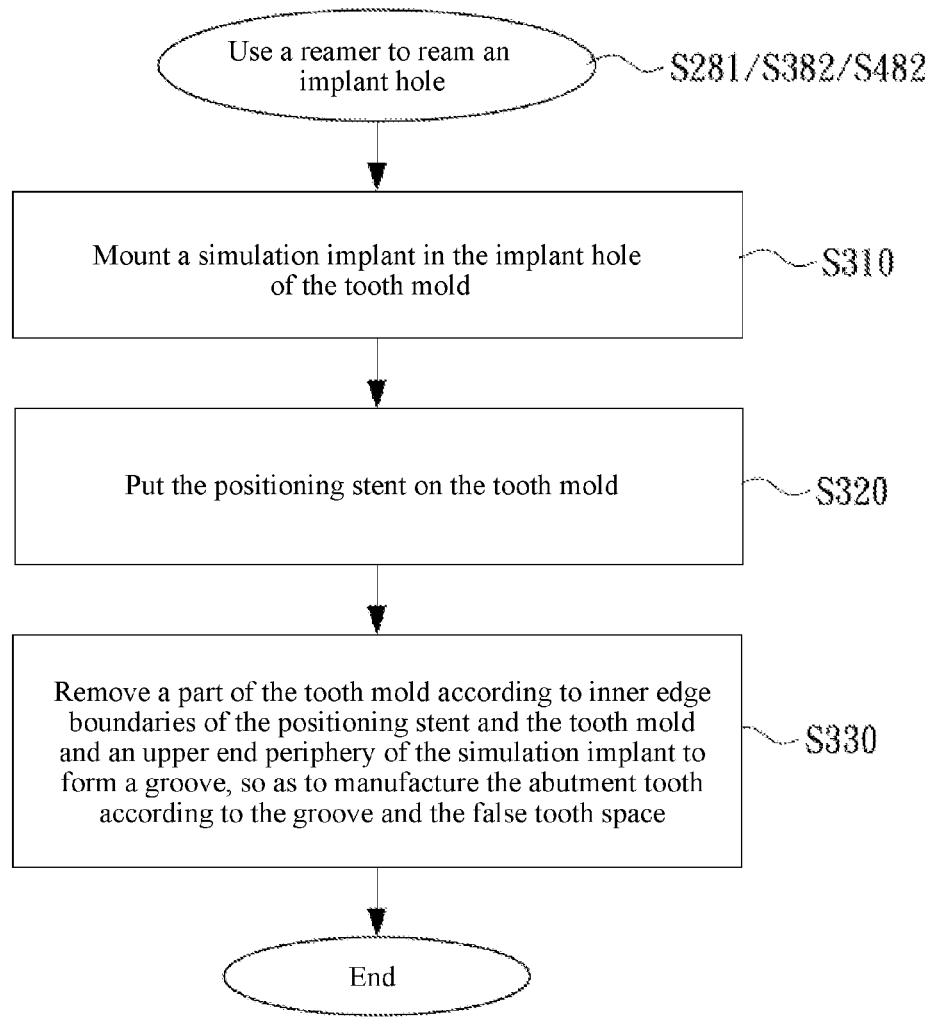
FIG. 18 is a flowchart according to a sixth embodiment.
Figure 19:
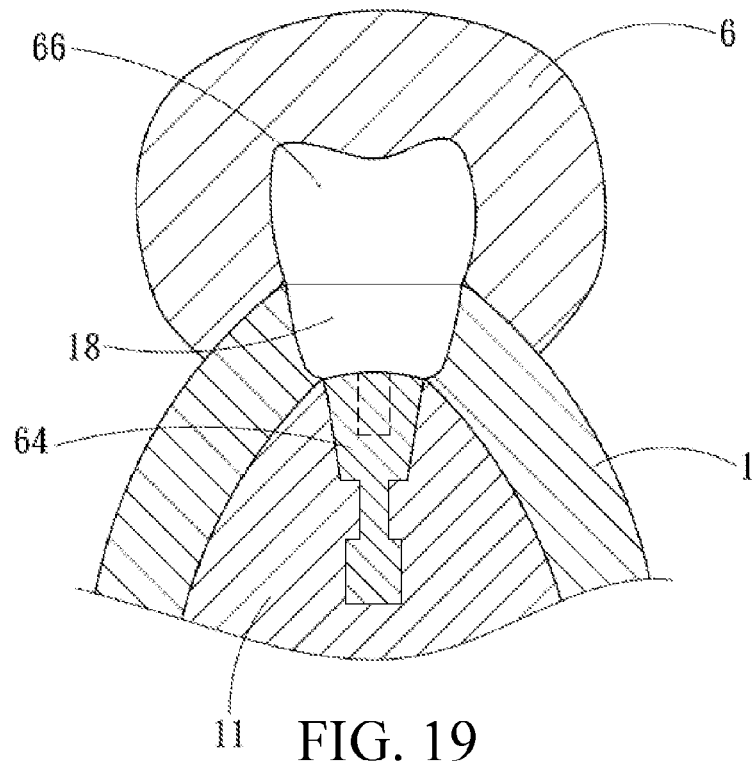
FIG. 19 is a first schematic view according to the sixth embodiment.
Figure 20:
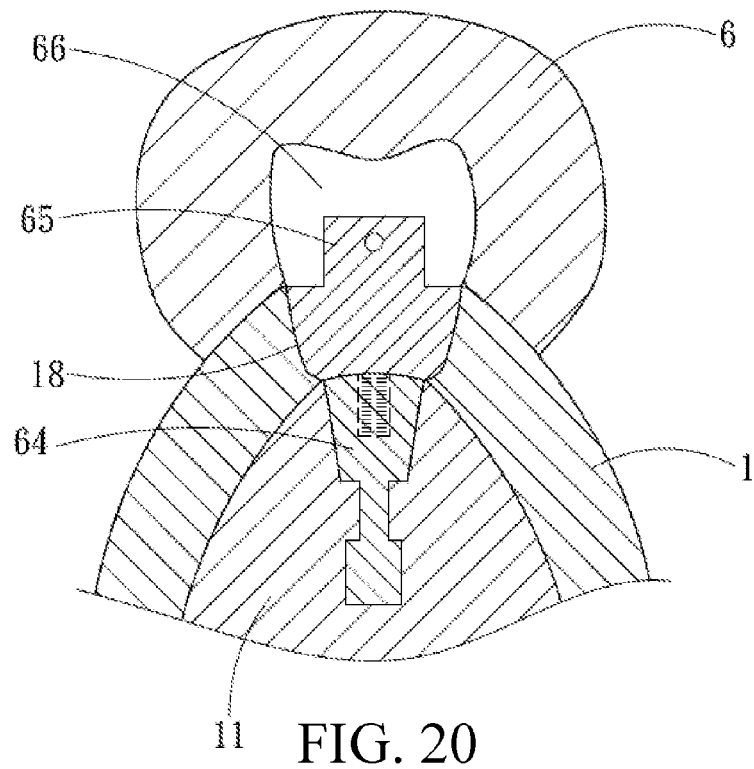
FIG. 20 is a second schematic view according to the sixth embodiment.
Figure 21:
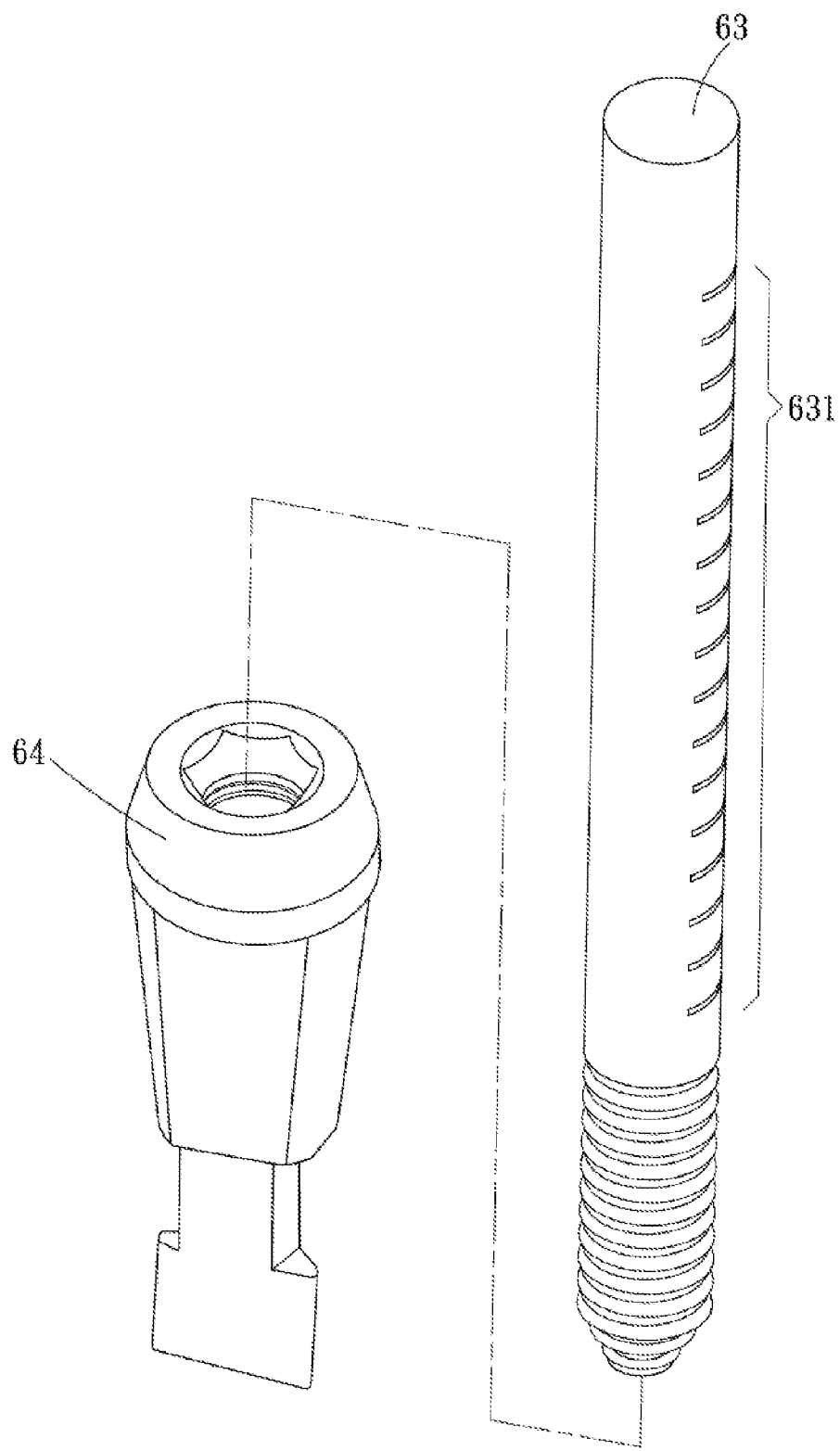
FIG. 21 is an analog implant conveyor according to the sixth embodiment.

FIG. 18 is a flowchart according to a sixth embodiment. FIG. 19 is a first schematic view according to the sixth embodiment, and FIG. 20 is a second schematic view according to the sixth embodiment. FIG. 21 is an analog implant conveyor 63 according to the sixth embodiment. Please refer to FIG. 18, FIG. 19, and FIG. 20, similar to Step S281, Step S382, or Step S482, the tooth mold 1 is used to replace the gum 1', and the implant hole 19 is drilled from the tooth mold 1. The disclosure provides a using method of the dental positioning stent, which is used to aid manufacturing of an abutment tooth 65. A shape of the positioning stent 6 corresponds to the tooth mold 1, and the positioning stent 6 has a false tooth space 66 corresponding to a shape of a false tooth. The using method includes the following steps.

In Step S310, an analog implant 64 is mounted in the implant hole 19 of the tooth mold 1. In some embodiments, the analog implant conveyor 63 shown in FIG. 21 may be locked to the analog implant 64 to replace the enlargement drill 8 shown in FIG. 11A, FIG. 13A, FIG. 14A, or FIG. 15A, so as to put the analog implant 64 in the implant hole 19 with the aid of the positioning stent 6.

Here, a diameter of the analog implant 64 is the same as that of the implant 14 preset to be mounted. After the analog implant 64 is placed in the implant hole 19, an upper end of the analog implant 64 is substantially located at a location corresponding to common boundaries of the actual gum and the actual alveolar bone 11. In order to determine an implant depth of the analog implant 64, the analog implant conveyor 63 has calibrations 631 corresponding to depths. In addition, another function of the calibrations 631 is for recognition of a rotation direction of the analog implant 64. Similarly, the calibrations 631 are also conducive to orientation of the abutment tooth 65 and the implant 14 in tooth implant surgery, so as to aid locking of the abutment tooth 65 and the implant 14.

In Step S320, the positioning stent 6 is put on the tooth mold 1. In some embodiments, the positioning stent 6 may be replaced with the positioning stent 6 manufactured in Step S140 or Step S240, or the false tooth coat.

In Step S330, a part of the tooth mold 1 is removed according to inner edge boundaries of the positioning stent 6 and the tooth mold 1 and an upper end periphery of the analog implant 64 to form a concave 18, so as to manufacture the abutment tooth 65 according to the concave 18 and the false tooth space 66.

Here, as shown in FIG. 20, through the embodiment and according to a shape of the concave 18 and the false tooth space, the abutment tooth 65 consistent with a gum of a patient is customized. In addition, before the tooth implant surgery is performed on the patient, the abutment tooth 65 and a false tooth corresponding to the abutment tooth 65 may be manufactured in advance. After the tooth implant surgery is completed, the patient can wear the abutment tooth 65 and the false tooth instantly, which is different from a conventional tooth implant process, in which after the implant 14 is implanted, the abutment tooth 65 and the false tooth are manufactured by repeated molding and cannot be worn until the wound heals.

In view of the above, the disclosure provides the dental positioning stent, and the manufacturing method, the using method, and the components for the same, which can actually aid the tooth implant positioning, drill and ream the implant hole accordingly in a reliable manner, aid the taking of the tomography image, and aid the dentist to evaluate the tooth implant surgery according to the tomography image and the tooth mold. Here, the components used in the dental positioning stent include the positioning aid 2, the positioning sleeve 3, the reaming sleeve 4, the positioning cap 5, the initial drill 7, the enlargement drill 8, the guide drill 9 or the shield 811.

While the disclosure has been described by the way of example and in terms of the preferred embodiments, it is to be understood that the disclosure need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A manufacturing method for a dental positioning stent, used for positioning an implant to mount an intended false tooth on the implant, the method comprising:
   manufacturing a tooth mold according to teeth in a mouth of a patient;
   selecting a preset implant position of the implant on the tooth mold;
   disposing a false tooth model, that is in equal proportion to the intended false tooth, on the tooth mold;
   selecting a preset slice plane passing through the preset implant position;
   slicing the tooth mold and the false tooth model along the preset slice plane;

fixing a first marker in the preset slice plane on a first side of the tooth mold and a first side of the false tooth model, wherein the first marker is impenetrable by an X-ray, the first side of the tooth mold and the first side of the false tooth model respectively located on a buccal surface of the tooth mold and a buccal surface of the false tooth model;

fixing a second marker in the preset slice plane on a second side of the tooth mold and a second side of the false tooth model, wherein the second marker is impenetrable by an X- ray, the second side of the tooth mold and the second side of the false tooth model respectively located on a lingual surface of the tooth mold and a lingual surface of the false tooth model;

covering the first and second markers, the false tooth model, and a part of the tooth mold so as to surround the first and second markers and the false tooth model with a shaping agent to form a positioning stent, wherein the shaping agent comprises a resin polymer and a developer;

putting the positioning stent on said teeth and a gum in the mouth of the patient;

performing tomography imaging with the positioning stent on said teeth and said gum, so as to acquire a slice image of the preset slice plane;

cutting the slice image along an edge of an image of the gum that is represented in the slice image so as to form a cut slice image comprising an image of an alveolar bone and the image of gum;

physically pasting the cut slice image on a slice plane of the tooth mold in equal proportion;

selecting a diameter, a length, an implant depth, and an implant angle of the implant according to the cut slice image that is pasted on the tooth mold, and a profile of the false tooth model;

mounting a slider in a positioning hole that is in a corresponding position of the positioning stent for the implant;

sliding the slider into the positioning hole when the positioning stent is positioned in the mouth of the patient; and guiding a drill with the slider.

2. The manufacturing method according to claim 1, wherein the selecting the preset implant position of the implant on the tooth mold comprises:

providing a positioning aid on the tooth mold, wherein an area of the tooth mold covered by the positioning aid is the same as that of the intended false tooth, a center of the positioning aid has the positioning hole, and the positioning hole runs through the positioning aid; and inserting the slider into the positioning hole of the positioning aid, and acquiring the preset implant position in a center of the slider.

3. The manufacturing method according to claim 1, wherein the drill is an initial drill, the slider is a positioning sleeve, and in the step of guiding the drill, the positioning sleeve guides the initial drill to drill a guide hole with a depth equal to the implant depth.

4. The manufacturing method according to claim 1, wherein the drill is an enlargement drill comprising a cutting portion and a shank portion, the slider is a reaming sleeve, and in the step of guiding the drill, the reaming sleeve guides the enlargement drill, such that the cutting portion reams a guide hole to form an implant hole.

5. The manufacturing method according to claim 1, wherein the drill is a guide drill comprising a cutting portion, a shank portion and a cylindrical portion extending from a bottom of the cutting portion, the cutting portion is connected between the shank portion and the cylindrical portion, a top of the cutting portion is flat, a diameter of the cylindrical portion is shorter than a longest width of the cutting portion, the slider is a reaming sleeve, and in the step of guiding the drill, the reaming sleeve guides the guide drill, such that the cylindrical portion is placed in advance into a guide hole and after the cylindrical portion is placed in advance into the guide hole, the cutting portion reams an upper end of the guide hole.

6. The manufacturing method according to claim 1, wherein the drill is an enlargement drill comprising a cutting portion, a shank portion and a connection part between the cutting portion and the shank portion, the slider is a positioning cap comprising a tube portion and a flat portion, the flat portion covering one end of the tube portion and having a drill bit guide hole in a center of the flat portion, and in the step of guiding the drill, the positioning cap guides the enlargement drill, such that he tube portion receives the enlargement drill and the flat portion of the positioning cap contacts with the connection part between the cutting portion and the shank portion of the enlargement drill, the shank portion passes through the drill bit guide hole, and the cutting portion reams another guide hole.

7. The manufacturing method according to claim 1, wherein the drill is a guide drill comprising a cutting portion, a shank portion and a cylindrical portion extending from a bottom of the cutting portion, the cutting portion is connected between the shank portion and the cylindrical portion, a top of the cutting portion is flat, a diameter of the cylindrical portion is shorter than a longest width of the cutting portion, the slider is a positioning cap comprising a tube portion and a flat portion, the flat portion covers one end of the tube portion, a center of the flat portion has a drill bit guide hole, and in the step of guiding the drill, the positioning cap guides the guide drill, such that the tube portion receives the guide drill, the shank portion passes through the drill bit guide hole, the cylindrical portion is placed in advance into another guide hole and after the cylindrical portion is placed in advance into the another guide hole, the cutting portion reams an upper end of the another guide hole.

8. The manufacturing method according to claim 1, wherein the first and second markers are a marking object located anywhere in the preset slice plane, and the marking object has a recognizable profile in a section of the preset slice plane.

9. A manufacturing method for a dental positioning stent, used to take a tooth tomography scanning slice image, the method comprising:

manufacturing a tooth mold according to teeth in a mouth, wherein the tooth mold comprises a dental crown portion and a gum portion;

selecting a preset slice plane of the tooth mold passing through the dental crown portion;

fixing a first marker in the preset slice plane on a first side of the tooth mold and contacting a buccal surface of the dental crown portion, wherein the marker is impenetrable by an X-ray;

fixing a second marker in the preset slice plane on a second side of the tooth mold and contacting a lingual surface of the dental crown portion, wherein the second marker is impenetrable by an X-ray; and covering the first and second markers and a part of the tooth mold surrounding the first and second markers with a shaping agent to form a positioning stent, wherein the shaping agent comprises a resin polymer and a developer.

10. The manufacturing method according to claim 9, wherein an end of the first marker directly contacts the dental crown portion,
- another end of the first marker directly contacts the gum portion,
- an end of the second marker directly contacts the dental crown portion, and
- another end of the second marker directly contacts the gum portion.

\* \* \* \* \*